(12) United States Patent
MacDonald et al.

(10) Patent No.: US 6,725,092 B2
(45) Date of Patent: Apr. 20, 2004

(54) ELECTROMAGNETIC RADIATION IMMUNE MEDICAL ASSIST DEVICE ADAPTER

(75) Inventors: Stuart G. MacDonald, Pultneyville, NY (US); Jeffrey L. Helfer, Webster, NY (US); Michael L. Weiner, Webster, NY (US)

(73) Assignee: Biophan Technologies, Inc., West Henrietta, NY (US)

(*) Notice: Subject to any disclaimer, the term of this patent is extended or adjusted under 35 U.S.C. 154(b) by 19 days.

(21) Appl. No.: 10/132,457

(22) Filed: Apr. 25, 2002

(65) Prior Publication Data

US 2003/0204207 A1 Oct. 30, 2003

(51) Int. Cl.$^7$ .................................................. A61N 1/00
(52) U.S. Cl. .......................................................... 607/2
(58) Field of Search ...................................... 607/1–156

(56) References Cited

U.S. PATENT DOCUMENTS

| | | |
|---|---|---|
| 3,057,356 A | 10/1962 | Greatbatch |
| 3,478,746 A | 11/1969 | Greatbatch |
| 3,508,167 A | 4/1970 | Russell, Jr. |
| 3,669,095 A | 6/1972 | Kobayashi et al. |
| 3,686,958 A | 8/1972 | Porter et al. |
| 3,718,142 A | 2/1973 | Mulier |
| 3,789,667 A | 2/1974 | Porter et al. |
| 3,825,015 A | 7/1974 | Berkovits |
| 4,012,641 A | 3/1977 | Brickerd, Jr. et al. |
| 4,041,954 A | 8/1977 | Ohara |
| 4,050,004 A | 9/1977 | Greatbatch |
| 4,071,032 A | 1/1978 | Schulman |
| 4,091,818 A | 5/1978 | Brownlee et al. |
| 4,200,110 A | 4/1980 | Peterson et al. |
| 4,210,029 A | 7/1980 | Porter |
| 4,254,776 A | 3/1981 | Tanie et al. |
| 4,325,382 A | 4/1982 | Miodownik |
| 4,333,053 A | 6/1982 | Harrison et al. |
| 4,341,221 A | 7/1982 | Testerman |
| 4,379,262 A | 4/1983 | Young |
| 4,432,363 A | 2/1984 | Kakegawa |
| 4,450,408 A | 5/1984 | Tiemann |
| 4,476,870 A | 10/1984 | Peterson et al. |
| 4,491,768 A | 1/1985 | Slicker |
| 4,611,127 A | 9/1986 | Ibrahim et al. |
| 4,677,471 A | 6/1987 | Takamura et al. |
| 4,686,964 A | 8/1987 | Yukoni et al. |
| 4,691,164 A | 9/1987 | Haragashira |
| 4,719,159 A | 1/1988 | Clark et al. |
| 4,727,874 A | 3/1988 | Bowers et al. |
| 4,763,075 A | 8/1988 | Weigert |
| 4,784,461 A | 11/1988 | Abe et al. |
| 4,798,443 A | 1/1989 | Knipe et al. |
| 4,800,883 A | 1/1989 | Winstrom |

(List continued on next page.)

FOREIGN PATENT DOCUMENTS

WO    WO 01/74241    10/2001

OTHER PUBLICATIONS

C. Roos, et al., "Fiber Optic Pressure Transducer for Use Near MR Magnetic Fields," RSNA 1985; one page.

K. Wickersheim et al., "Fiberoptic Thermometry and its Applications," J. Microwave Power (1987); pp. 85–94.

(List continued on next page.)

Primary Examiner—Scott M. Getzow
(74) Attorney, Agent, or Firm—Basch & Nickerson LLP; Michael J. Nickerson

(57) ABSTRACT

An electromagnetic radiation immune medical assist system includes a medical assist device; a photonic lead having a proximal end and a distal end; and an adapter to operatively connect the medical assist device with the photonic catheter. The adapter includes a housing, an interface to provide an operative communication connection between the adapter and the medical assist device, a transducer to convert information from the medical assist device into optical energy, and an optical interface to provide an operative connection between the adapter and the photonic catheter.

21 Claims, 15 Drawing Sheets

U.S. PATENT DOCUMENTS

| | | |
|---|---|---|
| 4,804,244 A | 2/1989 | Hasegawa et al. |
| 4,827,906 A | 5/1989 | Robicsek et al. |
| 4,827,934 A | 5/1989 | Ekwall |
| 4,858,610 A | 8/1989 | Callaghan et al. |
| 4,879,992 A | 11/1989 | Nishigaki et al. |
| 4,880,004 A | 11/1989 | Baker, Jr. et al. |
| 4,903,701 A | 2/1990 | Moore et al. |
| 4,911,525 A | 3/1990 | Hicks et al. |
| 4,930,521 A | 6/1990 | Metzger et al. |
| 4,934,785 A | 6/1990 | Mathis et al. |
| 4,987,897 A | 1/1991 | Funke |
| 4,991,590 A | 2/1991 | Shi |
| 5,010,888 A | 4/1991 | Jadvar et al. |
| 5,055,810 A | 10/1991 | deLaChapelle et al. |
| 5,058,586 A | 10/1991 | Heinze |
| 5,061,680 A | 10/1991 | Paulson et al. |
| 5,089,697 A | 2/1992 | Prohaska |
| 5,113,859 A | 5/1992 | Funke |
| 5,131,409 A | 7/1992 | Lobarev et al. |
| 5,154,387 A | 10/1992 | Trailer |
| 5,158,932 A | 10/1992 | Hinshaw et al. |
| 5,168,871 A | 12/1992 | Grevious |
| 5,178,149 A | 1/1993 | Imburgia et al. |
| 5,214,730 A | 5/1993 | Nagasawa et al. |
| 5,217,009 A | 6/1993 | Kronberg |
| 5,217,010 A | 6/1993 | Tsitlik et al. |
| 5,226,210 A | 7/1993 | Koskenmaki et al. |
| 5,240,004 A | 8/1993 | Walinsky et al. |
| 5,243,979 A | 9/1993 | Stein et al. |
| 5,265,602 A | 11/1993 | Anderson et al. |
| 5,267,564 A | 12/1993 | Barcel et al. |
| 5,324,310 A | 6/1994 | Greeninger et al. |
| 5,330,512 A | 7/1994 | Hauck et al. |
| 5,348,010 A | 9/1994 | Schnall et al. |
| 5,354,220 A | 10/1994 | Ganguly et al. |
| 5,370,668 A | 12/1994 | Shelton |
| 5,387,229 A | 2/1995 | Poore |
| 5,387,232 A | 2/1995 | Trailer |
| 5,402,070 A | 3/1995 | Shelton et al. |
| 5,410,413 A | 4/1995 | Sela |
| 5,415,653 A | 5/1995 | Wardle et al. |
| 5,425,373 A | 6/1995 | Causey, III |
| 5,435,308 A | 7/1995 | Gallup et al. |
| 5,435,316 A | 7/1995 | Kruse |
| 5,438,987 A | 8/1995 | Thacker et al. |
| 5,445,151 A | 8/1995 | Darrow et al. |
| 5,453,838 A | 9/1995 | Danielian et al. |
| 5,454,837 A | 10/1995 | Lindegren et al. |
| 5,456,698 A | 10/1995 | Byland et al. |
| 5,464,014 A | 11/1995 | Sugahara |
| 5,476,095 A | 12/1995 | Schnall et al. |
| 5,520,190 A | 5/1996 | Benedict et al. |
| 5,523,534 A | 6/1996 | Meister et al. |
| 5,569,158 A | 10/1996 | Suzuki et al. |
| 5,570,671 A | 11/1996 | Hickey |
| 5,574,811 A | 11/1996 | Bricheno et al. |
| 5,575,772 A | 11/1996 | Lennox |
| 5,582,170 A | 12/1996 | Soller |
| 5,590,227 A | 12/1996 | Osaka et al. |
| 5,601,611 A | 2/1997 | Fayram et al. |
| 5,603,697 A | 2/1997 | Grundy et al. |
| 5,604,433 A | 2/1997 | Theus et al. |
| 5,611,016 A | 3/1997 | Fangmann et al. |
| 5,619,605 A | 4/1997 | Ueda et al. |
| 5,626,618 A | 5/1997 | Ward et al. |
| 5,626,619 A | 5/1997 | Jacobson et al. |
| 5,631,988 A | 5/1997 | Swirhun et al. |
| 5,634,720 A | 6/1997 | Gallup et al. |
| 5,649,965 A | 7/1997 | Pons et al. |
| 5,653,735 A | 8/1997 | Chen et al. |
| 5,654,317 A | 8/1997 | Fujioka et al. |
| 5,658,966 A | 8/1997 | Tsukamoto et al. |
| 5,683,435 A | 11/1997 | Truex et al. |
| 5,697,958 A | 12/1997 | Paul et al. |
| 5,699,801 A | 12/1997 | Atalar et al. |
| 5,709,225 A | 1/1998 | Budgifvars et al. |
| 5,716,386 A | 2/1998 | Ward et al. |
| 5,723,856 A | 3/1998 | Yao et al. |
| 5,733,247 A | 3/1998 | Fallon |
| 5,738,105 A | 4/1998 | Kroll |
| 5,749,910 A | 5/1998 | Brumwell et al. |
| 5,752,977 A | 5/1998 | Grevious et al. |
| 5,755,739 A | 5/1998 | Sun et al. |
| 5,759,197 A | 6/1998 | Sawchuk et al. |
| 5,761,354 A | 6/1998 | Kuwano et al. |
| 5,766,227 A | 6/1998 | Nappholz et al. |
| 5,772,604 A | 6/1998 | Langberg et al. |
| 5,774,501 A | 6/1998 | Halpern et al. |
| 5,776,167 A | 7/1998 | Levine et al. |
| 5,776,168 A | 7/1998 | Gunderson |
| 5,782,241 A | 7/1998 | Felblinger et al. |
| 5,782,880 A | 7/1998 | Lahtinen et al. |
| 5,808,730 A | 9/1998 | Danielian et al. |
| 5,814,087 A | 9/1998 | Renirie |
| 5,814,089 A | 9/1998 | Stokes et al. |
| 5,814,090 A | 9/1998 | Latterell et al. |
| 5,814,091 A | 9/1998 | Dahlberg et al. |
| 5,817,130 A | 10/1998 | Cox et al. |
| 5,817,133 A | 10/1998 | Houben |
| 5,817,136 A | 10/1998 | Nappholz et al. |
| 5,818,990 A | 10/1998 | Steijer et al. |
| 5,827,195 A | 10/1998 | Lander |
| 5,827,997 A | 10/1998 | Chung et al. |
| 5,830,209 A | 11/1998 | Savage et al. |
| 5,836,895 A | 11/1998 | Ramsey, III |
| 5,865,839 A | 2/1999 | Doorish |
| 5,867,361 A | 2/1999 | Wolf et al. |
| 5,868,664 A | 2/1999 | Speier et al. |
| 5,869,412 A | 2/1999 | Yenni, Jr. et al. |
| 5,870,272 A | 2/1999 | Seifried et al. |
| 5,871,509 A | 2/1999 | Noren |
| 5,871,512 A | 2/1999 | Hemming et al. |
| 5,873,898 A | 2/1999 | Hemming et al. |
| 5,882,108 A | 3/1999 | Fraizer |
| 5,882,305 A | 3/1999 | Dumoulin et al. |
| 5,891,171 A | 4/1999 | Wickham |
| 5,895,980 A | 4/1999 | Thompson |
| 5,899,927 A | 5/1999 | Ecker et al. |
| 5,902,326 A | 5/1999 | Lessar et al. |
| 5,916,162 A | 6/1999 | Snelten et al. |
| 5,916,237 A | 6/1999 | Schu |
| 5,917,625 A | 6/1999 | Ogusu et al. |
| 5,919,135 A | 7/1999 | Lemelson |
| 5,928,145 A | 7/1999 | Ocali et al. |
| 5,928,270 A | 7/1999 | Ramsey, III |
| 5,928,570 A | 7/1999 | Reo |
| 5,940,554 A | 8/1999 | Chang et al. |
| 5,946,086 A | 8/1999 | Bruce |
| 5,951,596 A | 9/1999 | Bellinger |
| 5,954,660 A | 9/1999 | Legay et al. |
| 5,957,857 A | 9/1999 | Hartley |
| 5,963,034 A | 10/1999 | Mahapatra et al. |
| 5,963,690 A | 10/1999 | Cheng |
| 5,967,977 A | 10/1999 | Mullis et al. |
| 5,968,083 A | 10/1999 | Ciciarelli et al. |
| 5,973,779 A | 10/1999 | Ansari et al. |
| 5,973,906 A | 10/1999 | Stevenson et al. |
| 5,978,710 A | 11/1999 | Prutchi et al. |
| 5,982,961 A | 11/1999 | Pan et al. |
| 5,985,129 A | 11/1999 | Gough et al. |
| 5,987,995 A | 11/1999 | Sawatari et al. |

| | | |
|---|---|---|
| 5,999,853 A | 12/1999 | Stoop et al. |
| 5,999,857 A | 12/1999 | Weijand et al. |
| 6,005,191 A | 12/1999 | Tzeng et al. |
| 6,011,994 A | 1/2000 | Kronberg |
| 6,013,376 A | 1/2000 | Yenni, Jr. |
| 6,016,448 A | 1/2000 | Busacker et al. |
| 6,016,477 A | 1/2000 | Ehnebuske et al. |
| 6,023,641 A | 2/2000 | Thompson |
| 6,024,738 A | 2/2000 | Daikuzono et al. |
| 6,026,316 A | 2/2000 | Kucharczyk |
| 6,029,086 A | 2/2000 | Kim et al. |
| 6,029,087 A | 2/2000 | Wohlgemuth |
| 6,031,710 A | 2/2000 | Wolf et al. |
| 6,036,639 A | 3/2000 | Allred, III et al. |
| 6,036,654 A | 3/2000 | Quinn et al. |
| 6,044,301 A | 3/2000 | Hartlaub et al. |
| 6,052,613 A | 4/2000 | Takaki |
| 6,052,614 A | 4/2000 | Morris, Sr. et al. |
| 6,052,623 A | 4/2000 | Fenner et al. |
| 6,055,455 A | 4/2000 | O'Phelan et al. |
| 6,056,415 A | 5/2000 | Allred, III et al. |
| 6,056,721 A | 5/2000 | Shulze |
| 6,064,906 A | 5/2000 | Langberg et al. |
| 6,066,096 A | 5/2000 | Smith et al. |
| 6,067,472 A | 5/2000 | Vonk et al. |
| 6,076,003 A | 6/2000 | Rogel |
| 6,080,829 A | 6/2000 | Tapsak et al. |
| 6,090,473 A | 7/2000 | Yoshikawa et al. |
| 6,090,728 A | 7/2000 | Yenni, Jr. et al. |
| 6,091,015 A | 7/2000 | delValle et al. |
| 6,091,744 A | 7/2000 | Sorin et al. |
| 6,091,987 A | 7/2000 | Thompson |
| 6,101,973 A | 8/2000 | Stewart et al. |
| 6,118,910 A | 9/2000 | Chang |
| 6,119,031 A | 9/2000 | Crowley |
| 6,134,003 A | 10/2000 | Tearney et al. |
| 6,134,478 A | 10/2000 | Spehr |
| 6,142,678 A | 11/2000 | Cheng |
| 6,144,205 A | 11/2000 | Souza et al. |
| 6,144,866 A | 11/2000 | Miesel et al. |
| 6,144,881 A | 11/2000 | Hemming et al. |
| 6,146,415 A | 11/2000 | Fitz |
| 6,148,222 A | 11/2000 | Ramsey, III |
| 6,148,229 A | 11/2000 | Morris, Sr. et al. |
| 6,149,313 A | 11/2000 | Giebel et al. |
| 6,163,724 A | 12/2000 | Hemming et al. |
| 6,166,806 A | 12/2000 | Tjin |
| 6,169,921 B1 | 1/2001 | Ken Knight et al. |
| 6,171,240 B1 | 1/2001 | Young et al. |
| 6,173,203 B1 | 1/2001 | Barkley et al. |
| 6,179,482 B1 | 1/2001 | Takizawa et al. |
| 6,188,926 B1 | 2/2001 | Vock |
| 6,192,261 B1 | 2/2001 | Gratton et al. |
| 6,198,968 B1 | 3/2001 | Prutchi et al. |
| 6,198,972 B1 | 3/2001 | Hartlaub et al. |
| 6,208,899 B1 | 3/2001 | Kroll |
| 6,216,041 B1 | 4/2001 | Tierney et al. |
| 6,223,083 B1 | 4/2001 | Rosar |
| 6,226,545 B1 | 5/2001 | Gilderdale |
| 6,230,060 B1 | 5/2001 | Mawhinney |
| 6,236,879 B1 | 5/2001 | Konings |
| 6,238,686 B1 | 5/2001 | Burrell et al. |
| 6,240,317 B1 | 5/2001 | Villaseca et al. |
| 6,245,020 B1 | 6/2001 | Moore et al. |
| 6,246,910 B1 | 6/2001 | Bonnet et al. |
| 6,247,474 B1 | 6/2001 | Greeninger et al. |
| 6,254,632 B1 | 7/2001 | Wu et al. |
| 6,256,537 B1 | 7/2001 | Stoop et al. |
| 6,256,541 B1 | 7/2001 | Heil et al. |
| 6,258,087 B1 | 7/2001 | Edwards et al. |
| 6,259,843 B1 | 7/2001 | Kondo |
| 6,259,954 B1 | 7/2001 | Conger et al. |
| 6,263,229 B1 | 7/2001 | Atalar et al. |
| 6,263,242 B1 | 7/2001 | Mika et al. |
| 6,266,555 B1 | 7/2001 | Werner et al. |
| 6,266,563 B1 | 7/2001 | Ken Knight et al. |
| 6,266,564 B1 | 7/2001 | Hill et al. |
| 6,266,566 B1 | 7/2001 | Nichols et al. |
| 6,270,457 B1 | 8/2001 | Bardy |
| 6,270,831 B2 | 8/2001 | Kumar et al. |
| 6,272,377 B1 | 8/2001 | Sweeney et al. |
| 6,272,380 B1 | 8/2001 | Warman et al. |
| 6,274,265 B1 | 8/2001 | Kraska et al. |
| 6,275,730 B1 | 8/2001 | Ken Knight et al. |
| 6,275,732 B1 | 8/2001 | Hsu et al. |
| 6,275,734 B1 | 8/2001 | McClure et al. |
| 6,277,078 B1 | 8/2001 | Porat et al. |
| 6,277,107 B1 | 8/2001 | Lurie et al. |
| 6,278,057 B1 | 8/2001 | Avellanet |
| 6,278,277 B1 | 8/2001 | Zeiger |
| 6,278,894 B1 | 8/2001 | Salo et al. |
| 6,278,897 B1 | 8/2001 | Rutten et al. |
| 6,296,654 B1 | 10/2001 | Ward |
| 6,367,984 B1 | 4/2002 | Stephenson et al. |

OTHER PUBLICATIONS

Mark B. M. Hofman; "MRI–Compatible Cardiac Pacing Catheter," JMRI; May/Jun. 1997; p. 612.

A.A. Damji et al.,"RF Interference Suppression in a Cardiac Synchronization System Operating in High Magnetic Field NMR Imaging System," Magnetic Resonance Imaging, vol. 6, pp 637–640, (1988).

Frank G. Shellock et al., "Burns Associated with the use of Monitoring Equipment during MR Procedures,"JMRI, Jan./Feb. 1996; pp. 271–272.

J. Nyenhuis et al., "Heating Near Implanted Medical Devices by the MRI RF–Magnetic Field," IEEE Trans. Mag.; Sep. 1999; four pages.

Frank Shellock et al., "Cardiovascular Catheters and Accessories: Ex Vivo Testing of Ferromagnetism, Heating, and Artifacts Associated with MRI," JMRI, Nov./Dec. 1998, vol. 8 #6; pp. 1338–1342.

J. Rod Gimbel et al., "Safe Performance of Magnetic Resonance," PACE; vol. 19; Jun. 1996; pp. 913–919.

National Library Of Medicine; "Rapid Ventricular Pacing in a Pacemaker Patient Undergoing Magnetic Resonance Image," Pub Med; Pacing Clin Electrophysiol; Jun. 1998; p. 1.

National Library Of Medicine;"Effects of Magnetic Resonance Imaging on Cardiac Pacemakers and Electrodes," pub Med; Am Heart J; (1997); pp. 1–2.

M. Kusumoto et al., "Cardiac Pacing for the Clinician," Lippincott Williams & Wilkins; (2001); Chapter 1, pp. 9, 12, 13, 18, 22, 14.

Donald Fink; "Electronic Engineering," Electronic Engineers Handbook; 2nd edition, Mcgraw Hill; (1982); Section 14; pp. 29–45.

X Luo et al., "Electromagnetic Interference Shielding Using Carbon–Fiber Carbon–Matrix and Polymer–Matrix Composites," Composites Part B: Engineering; (1999); pp. 227–231.

D.D.L. Chung, "Flexible Graphite for Gasketing, Absorption, Electromagnetic Interference Shielding, Vibration Damping, Electrochemical Applications, and Stress Sensing," Journal of Materials Engineering and Performance; Apr. 2000; vol. 9 p. 161–163.

M. Konings et al., "Catheters and Guidewires in Interventional MRI; Problems and Solutions," Medical Mundi; 45/1; Mar. (2001).

M. Konings; "Development of an MR–Safe Tracking Catheter with a Laser DrivenTip Coil," Journal of Magnetic Resonance Imaging 2001:13:131–135. c. 2001 Wiley–Liss, Inc.

Ey Yong et al., "An Optical System for Wireless Detuning of Parallel Resonant Circuits" Journal of Magnetic Resonance Imaging; (2000); vol. 12, pp. 632–638.

Bernd Nowak; "Taking Advantage of Sophisticated Pacemaker Diagnostics," Excerpta Medica; (1999); pp. 172D–179D.

Jose A. Jogler et al., "Interaction of a Commercial Heart Rate Monitor With Implanted Pacemakers," Excerpta Medica; (1999); pp. 790–792.

J.A. Pomposo et al., "Polypyrrole–based Conducting Hot Melt Adhesives for EMI Shielding Applications," Elsevier; Synthetic Metals 104; (1999); pp. 107–111.

K. Grattan et al., "Fiber Optic Sensor Technology: An Overview," Elsevier; Sensors and Actuators 82; (2000);pp. 40–61.

L. Rippert et al., "Optical and Acoustic Damage Detection in Laminated CFRP Composite Materials," Elsevier; Composites Science and Technology 60; (2000); pp. 2713–2724.

C. Strandman et al., "A Production Process of Silicon Sensor Elements for a Fibre–Optic Pressure Sensor," Elsevier; Sensors and Actuators A63; (1997); pp. 69–74.

D. Howard et al., "A Single–Fringe Etalon Silicon Pressure Transducer," Elsevier; Sensors and Actuators 86; (2000); pp. 21–25.

Dan Haronian, "Displacement Sensing Using Geometrical Modulation in Reflection Mode (GM–RM) of Coupled Optical Waveguides," J. Micromech, Microeng., (UK), (1998); pp. 323–326.

H Ghafouri–Shiraz, "A Novel Distributed Feedback Laser Diode Structure foran Optical Wavelength Tunable Filter," Semicond. Sci. Technol. 12; (UK), (1997); pp. 1161–1165.

L. Kasarian, "A New Optical Fiber Multiplexer for Distortion–Free Light Transfer in Multichannel Fiber Optic Sensor Systems," Elsevier; Sensors and Actuators 84; (2000); pp. 250–258.

X. Yan et al., "Electric Field Controlled 2×2 Bypass Exchange Photorefractive Switch," IOP Publishing; (UK) (1998), pp. 383–386.

E. Piener et al., "A Micromachined Vibration Sensor Based on the Control of Power Transmitted Between Optical Fibres," Elsevier; Sensors and Actuators A65; (1998) pp. 23–29.

Engin Molva; "Microchip Lasers and Their Applications in Optical Microsystems," Elsevier; Optical Materials 11; (1999); pp. 289–299.

D. Sun et al., "High Performance Unidirectional Electrooptic Modulator Based On Polymeric Highly Multi–Mode Waveguides,"Elsevier; Optics & Laser Technology 30; (1998); 481–489.

Engin Molva; "Microchip Lasers and Their Applications In Optical Microsystems," Elsevier; Optical Materials 11; (1999); pp. 289–299.

J. Linares et al., "Theory and Design of an Integrated Optical Sensor Based on Planar Waveguiding Lenses," Elsevier; Optics Communications 180; (2000); pp. 29–36.

O. Parriaux et al., "Coupling Gratings as Waveguide Functional Elements," IOP Publishing; Pure Appl. Opt. 5; (1996); pp. 453–469.

E T Enikov et al., "Three–Dimensional Microfabrication for a Multi– Degree of Freedom Capacitive Force Sensor Using Fibre–Chip Coupling" IOP Publishing; (UK); J. Micromechl. Microeng. 10;(2000) pp. 492–497.

J. Holm et al., "Through–Etched Silicon Carriers for Passive Alighnment of Optical Fibers to Surface–Active Optoelectronic Components" Elsevier;Sensors and Actuators 82; (2000) pp. 245–248.

M. Kimura et al., "Vibration Sensor Using Optical–Fiber Catilever with Bulb–Lens" Elsevier; Sensors and Actuators A66; (2000) pp. 178–183.

Y. Mao et al., "Three–Stage Wavelength Converter Based on Cross–Grain Modulation in Semiconductor Optical Amplifiers"Elsevier; Optics Communications 167; (1999) pp. 57–66.

X. Hu et al., "Dynamically Induced Irreversibility: Light Amplification and Quantum Noise Reduction in a V–Type Three–Level System" IOP Publishing; J. Opt. B: Quantum Semiclass. Opt. 2; (UK) (2000); pp. 570–575.

Y. Yim et al., "Lithium Niobate Integrated–Optic Voltage Sensorwith Variable Sensing Ranges" Elsevier; Optics Communications 152; Jul. 1, 1998; pp. 225–228.

C. Lee et al., "Electromagnetic Interference Shilding Efficiency of Polyaniline Mixtures and Multilayer Films" Elsevier; Synthetic Metals 102; (1999) pp. 1346–1349.

Marc Desmulliez, "Optoelectronics–VLSI System Integration Technological Challenges" Elsevier; Materials Science and Engineering B74;(2000) pp. 269–275.

J. Zook et al., "Fiber–optic Vibration Sensor Baed on Frequency Modulation of Light–Excited Oscillators" Elsevier; Sensors and Actuators 83; (2000); pp. 270–276.

M. Reta–Hernandez et al., "Attenuation of Low Frequency Magnetic Fields Using Active Shielding" Elsevier; Electric Power Systems Research 45; (1998); pp. 57–63.

C. Huang et al., "The EMI Shielding Effectiveness of PC/ABS/Nickel–Coated Carbon–Fibre Composites" Elsevier; European Polymer Journal 36; (2000) pp. 2727–2737.

A. Jerwzewski et al.;, "Development of an MRI–Compatible Catheter for Pacing the Heart: Initial In Vitro and In Vivo Results," JMRI, ISHRM (US), vol. 6 (No. 6), p. 948–949, ( Jun. 14, 1996).

W. Moshage et al., "A Non–Magnetic, MRI Compatible Pacing Center for Clinical Application in Magnetocardiography," Biomedizinixche Technik Band, Erganzungsband (Germany), p. 162–163, ( Jun. 14, 1990).

ELECTROMAGNETIC RADIATION IMMUNE MEDICAL ASSIST DEVICE ADAPTER

CROSS REFERENCE TO RELATED PATENT APPLICATIONS

The subject matter of co-pending U.S. patent application Ser. No. 09/885,867, filed on Jun. 20, 2001, entitled "Controllable, Wearable MRI-Compatible Cardiac Pacemaker With Pulse Carrying Photonic Catheter And VOO Functionality", co-pending U.S. patent application Ser. No. 09/885,868, filed on Jun. 20, 2001, entitled "Controllable, Wearable MRI-Compatible Cardiac Pacemaker With Power Carrying Photonic Catheter And VOO Functionality"; co-pending U.S. patent application Ser. No. 10/037,513, filed on Jan. 4, 2002, entitled "Optical Pulse Generator For Battery Powered Photonic Pacemakers And Other Light Driven Medical Stimulation Equipment"; co-pending U.S. patent application Ser. No. 10/037,720, filed on Jan. 4, 2002, entitled "Opto-Electric Coupling Device For Photonic Pacemakers And Other OptoElectric Medical Stimulation Equipment"; co-pending U.S. patent application Ser. No. 09/943,216, filed on Aug. 30, 2001, entitled "Pulse Width Cardiac Pacing Apparatus"; co-pending U.S. patent application Ser. No. 09/964,095, filed on Sep. 26, 2001, entitled "Process for Converting Light"; co-pending U.S. patent application Ser. No. 09/921,066, filed on Aug. 2, 2001, entitled "MRI-Resistant Implantable Device"; co-pending U.S. patent application Ser. No. 10/077,842, filed on Feb. 19, 2002, entitled "An Electromagnetic Interference Immune Tissue Invasive System"; co-pending U.S. patent application Ser. No. 10/077,823, filed on Feb. 19, 2002, entitled "An Electromagnetic Interference Immune Tissue Invasive System"; co-pending U.S. patent application Ser. No. 10/077,887, filed on Feb. 19, 2002, entitled "An Electromagnetic Interference Immune Tissue Invasive System"; copending U.S. patent application Ser. No. 10/077,883, filed on Feb. 19, 2002, entitled "An Electromagnetic Interference Immune Tissue Invasive System"; and co-pending U.S. patent application Ser. No. 10/077,958, filed on Feb. 19, 2002, entitled "An Electromagnetic Interference Immune Tissue Invasive System".

The entire content of each of the above noted co-pending U.S. patent applications (Ser. Nos.: 09/885,867; 09/885,868; 10/037,513; 10/037,720; 09/943,216; 09/964,095; 09/921,066; 10/077,842; 10/077,823; 10/077,887; 10/077,883; and 10/077,958) is hereby incorporated by reference.

FIELD OF THE INVENTION

The present invention relates generally to tissue and organ stimulating and sensing devices, and more particularly, to a medical adapter for providing connectivity between a cardiac pacer and associated pacer leads and for controlling the operation of the cardiac pacer. The present invention also relates to a medical adapter capable of sending stimulating signals to and receiving sensing signals from a patient's heart.

BACKGROUND OF THE PRESENT INVENTION

Cardiac pacers, which provide stimulation to a patient's heart, by means of amplitude and frequency modulated electrical pulses, have been developed for permanent or temporary applications. The two most common types of cardiac pacers currently in use are pacemakers and implantable cardioverter-defibrillators (ICD). Cardiac pacers can be implanted in a suitable location inside the patient's body or located outside the patient's body. Cardiac pacers operate with one or more conductive leads, which carry stimulating, low voltage electrical pulses, generated by the pacer, to selected sites within the patient's heart, to communicate sensing signals from those sites back to the cardiac pacer, and to carry high energy pulses, generated by an ICD, to defibrillate the heart, if required.

Furthermore, it is often necessary to provide stimulation of a patient's heart using a cardiac pacer located outside the patient's body or to provide temporary stimulation of the patient's heart.

Such is the case, when a physician might want to try more than one cardiac pacer before selecting the most appropriate one for permanent implantation. To enable the physician to try more than one cardiac pacer before selecting the most appropriate one for permanent implantation, medical cardiac adapters have been developed. These adapters allow a physician to connect various pacers to the patient's hearts via implanted leads wherein the various pacers may have different interfaces for connecting to the leads. The adapters provide the universal interface between the implanted leads and the pacer so as to provide interchangeability between the pacers. Examples of such previously proposed adapters are disclosed in the following patents.

The Bourney et al. Patent (U.S. Pat. No. 4,545,381) discloses and claims an adapter for converting an implantable cardiac pacer to an externally worn cardiac pacer. This adapter provides a housing to which a cardiac pacer can be secured. It also provides compatibility with a plurality of cardiac pacers.

The Fain et al. Patent (U.S. Pat. No. 5,679,026) discloses and claims a header adapter, which is designed to fit onto the header and case of a cardiac pacer. This header adapter provides a plurality of lead connector configurations, thereby allowing the use of different types of leads and compatibility between leads and cardiac pacers from different manufacturers.

It is also often necessary to maintain proper stimulation of a patient's heart with an external pacer while the patient is undergoing medical procedures. However, certain medical procedures, such as Magnetic Resonance Imaging (MRI), can interfere with the proper stimulation of a patient's heart with an external pacer and implanted leads.

MRI is an imaging technique adapted to obtain both images of anatomical features of human patients as well as some aspects of the functional activities of biological tissue. These images have medical diagnostic value in determining the state of the health of the tissue examined.

In an MRI procedure, a patient is typically aligned to place the portion of the patient's anatomy to be examined in the imaging volume of the MRI apparatus. Such an MRI apparatus typically comprises a primary magnet for supplying a constant magnetic field ($B_0$) which, by convention, is along the z-axis and is substantially homogeneous over the imaging volume and secondary magnets that can provide linear magnetic field gradients along each of three principal Cartesian axes in space (generally x, y, and z, or $x_1$, $x_2$ and $x_3$, respectively). A magnetic field gradient ($B_0/x_i$) refers to the variation of the field along the direction parallel to $B_0$ with respect to each of the three principal Cartesian axes, $x_i$. The apparatus also comprises one or more RF (radio frequency) coils which provide excitation and detection of the MRI signal.

The use of MRI with patients who require medical assist devices, such as external cardiac assist devices or other external medical assist devices that also utilize implanted leads to stimulate a certain tissue region or organ, often presents problems. As is known to those skilled in the art, devices such as pulse generators (IPGs) and cardioverter/defibrillator/pacemakers (CDPs) are sensitive to a variety of forms of electromagnetic interference (EMI) because these enumerated devices include sensing and logic systems that respond to low-level electrical signals emanating from the monitored tissue region of the patient. Since the sensing systems and conductive elements of these devices are responsive to changes in local electromagnetic fields, the devices are vulnerable to external sources of severe electromagnetic noise, and in particular, to electromagnetic fields emitted during the MRI procedure. Thus, patients with such devices are generally advised not to undergo MRI procedures.

To more appreciate the problem, the use of a cardiac assist device during a MRI process will be briefly discussed.

The human heart may suffer from two classes of rhythmic disorders or arrhythmias: bradycardia and tachyarrhythmia. Bradycardia occurs when the heart beats too slowly, and may be treated by a common pacemaker delivering low voltage (about 3 V) pacing pulses having a duration of about 1 millisecond.

The common pacemaker operates in conjunction with one or more electrically conductive leads, adapted to conduct electrical stimulating pulses to sites within the patient's heart, and to communicate sensed signals from those sites back to the device.

Furthermore, the common pacemaker typically has a metal case and a connector block mounted to the metal case that includes receptacles for leads which may be used for electrical stimulation or which may be used for sensing of physiological signals. Electrical interfaces are employed to connect the leads outside the metal case with the medical device circuitry and the battery inside the metal case.

Electrical interfaces serve the purpose of providing an electrical circuit path extending from the interior of a sealed metal case to an external point outside the case while maintaining the seal of the case. A conductive path is provided through the interface by a conductive pin that is electrically insulated from the case itself.

Such interfaces typically include a ferrule that permits attachment of the interface to the case, the conductive pin, and a hermetic glass or ceramic seal that supports the pin within the ferrule and isolates the pin from the metal case.

A common pacemaker can, under some circumstances, be susceptible to electrical interference such that the desired functionality of the pacemaker is impaired. For example, common pacemaker requires protection against electrical interference from electromagnetic interference (EMI), defibrillation pulses, electrostatic discharge, or other generally large voltages or currents generated by other devices external to the medical device. As noted above, more recently, it has become crucial that cardiac assist systems be protected from intense magnetic and radio frequency (RF) fields associated with MRI.

Such electrical interference can damage the circuitry of the cardiac assist systems or cause interference in the proper operation or functionality of the cardiac assist systems. For example, damage may occur due to high voltages or excessive currents introduced into the cardiac assist system.

Therefore, it is required that such voltages and currents be limited at the input of such cardiac assist systems, e.g., at the interface. Protection from such voltages and currents has typically been provided at the input of a cardiac assist system by the use of one or more zener diodes and one or more filter capacitors.

For example, one or more zener diodes may be connected between the circuitry to be protected, e.g., pacemaker circuitry, and the metal case of the medical device in a manner which grounds current surges through the diode(s). Such zener diodes and capacitors used for such applications may be in the form of discrete components mounted relative to circuitry at the input of a connector block where various leads are connected to the medical device, e.g., at the interfaces for such leads.

However, such protection, provided by zener diodes and capacitors placed at the input of the medical device, increases the congestion of the medical device circuits, requiring at least one zener diode and one capacitor per input/output connection or interface. This is contrary to the desire for increased miniaturization of medical devices.

Further, when such protection is provided, interconnect wire length for connecting such protection circuitry and pins of the interfaces to the medical device circuitry that performs desired functions for the medical device tends to be undesirably long. The excessive wire length may lead to signal loss and undesirable inductive effects. The wire length can also act as an antenna that conducts undesirable electrical interference signals to sensitive ceramic metal oxide semiconductor (CMOS) circuits within the medical device to be protected.

Additionally, the radio frequency (RF) energy that is inductively coupled into the wire causes intense heating along the length of the wire, and at the electrodes that are attached to the heart wall. This heating may be sufficient to ablate the interior surface of the blood vessel through which the wire lead is placed, and may be sufficient to cause scarring at the point where the electrodes contact the heart. A further result of this ablation and scarring is that the sensitive node that the electrode is intended to pace with low voltage signals becomes desensitized, so that pacing the patient's heart becomes less reliable, and in some cases fails altogether.

A conventional solution for protecting a medical device from electromagnetic interference is illustrated in FIG. 1 that is a schematic view of a medical device 12 embodying protection against electrical interference. At least one lead 14 is connected to the medical device 12 in connector block region 13 using an interface.

In the case where medical device 12 is a pacemaker, the pacemaker 12 includes at least one or both of pacing and sensing implanted leads represented generally as leads 14 to sense electrical signals attendant to the depolarization and repolarization of the heart 16, and to provide pacing pulses for causing depolarization of cardiac tissue in the vicinity of the distal ends thereof.

FIG. 2 more particularly illustrates the circuit that is used conventionally to protect from electromagnetic interference. As shown in FIG. 2, protection circuitry 150 is provided using a diode array component 130. The diode array consists of five zener diode triggered silicon controlled rectifiers (SCRs) with anti-parallel diodes arranged in an array with one common connection. This allows for a small component size despite the large currents that may be carried through the device during defibrillation, e.g., 10 amps. The SCRs 120–124 turn on and limit the voltage across the device when excessive voltage and current surges occur.

As shown in FIG. 2, the zener diode triggered SCRs 120, 121, 123, and 124 are connected to an electrically conductive pin 125, 126, 128, and 129. Further, the electrically conductive pin 125, 126, 128, and 129 are connected to medical device contact regions 131, 132, 134, and 135 to be wire bonded to pads of a printed circuit board. The diode array component 130 is connected to the electrically conductive pins 125, 126, 128, and 129 via the die contact regions along with other electrical conductive traces of the printed circuit board.

As seen above, these conventional approaches fail to provide a method to protect a medical assist device system having implanted leads and using an adapter to coupled the implanted leads to the medical assist device, such as a pacer, during a MRI procedure.

Thus, there is a need to provide an adapter for a cardiac pacing system, which offers a modular approach to connectivity between cardiac pacers and cardiac leads. Moreover, there is a need to provide protection against electromagnetic interference, without requiring much circuitry and to provide fail-safe protection against radiation produced by magnetic resonance imaging (MRI) procedures. Further, there is a need to provide devices that prevent the possible damage that can be done at the tissue interface due to electromagnetic interference or insult. Furthermore, there is a need to provide an effective means for transferring energy from one point of the body to another point without having the energy causing a detrimental effect upon the body.

SUMMARY OF THE INVENTION

One aspect of the present invention is a photonic adapter to provide an operational electrical interface between a medical assist device and a photonic catheter. The photonic adapter includes a housing; an electrical interface to provide an operative connection between the photonic adapter and the medical assist device; and a photonic transducer to convert electrical energy from the medical assist device to optical energy, the optical energy being utilized by the photonic catheter.

Another aspect of the present invention is a photonic adapter to provide an operational transmitter/receiver interface between a medical assist device and a photonic catheter. The photonic adapter includes a housing; a transmitter/receiver interface to provide an operative communication connection between the adapter and the medical assist device; and a transducer to convert information from the medical assist device into optical energy.

A third aspect of the present invention is an electromagnetic radiation immune medical assist system. The electromagnetic radiation immune medical assist system includes a medical assist device; a photonic lead having a proximal end and a distal end; and an adapter to operatively connect the medical assist device with the photonic catheter. The adapter includes a housing, an interface to provide an operative communication connection between the adapter and the medical assist device, and a transducer to convert information from the medical assist device into optical energy.

A fourth aspect of the present invention is an adaptive bridge for providing an interface between a photonic adapter and a medical assist device. The adaptive bridge includes a first interface to provide an electrical connection between the adaptive bridge and the medical assist device; a second interface to provide an electrical connection between the adaptive bridge and the photonic adapter; and a passive electrical lead to provide an electrical conduit between the first interface and the second interface.

A fifth aspect of the present invention is a medical assist system. The medical assist system includes a medical assist device; a photonic adapter; and an adaptive bridge for providing an interface between the photonic adapter and the medical assist device.

BRIEF DESCRIPTION OF THE DRAWINGS

The present invention may take form in various components and arrangements of components, and in various steps and arrangements of steps. The drawings are only for purposes of illustrating a preferred embodiment and are not to be construed as limiting the present invention, wherein.

DETAILED DESCRIPTION OF THE PRESENT INVENTION

For the purposes of the description below and the appended claims, the term, medical assist device, refers to any device that may enable monitoring of living tissue(s) or living system(s) wherein the monitoring may be, but not limited to an EKG signal, an ECG signal, a glucose level, hormone level, or cholesterol level. The medical assist device may also enable stimulus intervention to provide assistance to living tissue(s) or living system(s) so that the stimulus causes the selected body tissue or system to function as desired. The stimulus may be, but not limited to, a cardiac stimulating substance or electrical pulse, a blood thinning substance, insulin, estrogen, progesterone, or testosterone. Furthermore, the medical assist device may be implanted in a body cavity of a living organism, either. temporarily or permanently, or subcutaneously implanted into a living organism either temporarily or permanently. Moreover, the medical assist device may be located external to the living organism. Examples of medical assist devices are, but not limited to, wearable or implantable cardiac pacers (such as pacemakers), implantable pulse generators (IPGs), cardioverter/defibrillator/pacemakers (CDPs), cardiac monitoring systems, insulin pump controllers, brain monitoring systems, etc.

Figure 1:
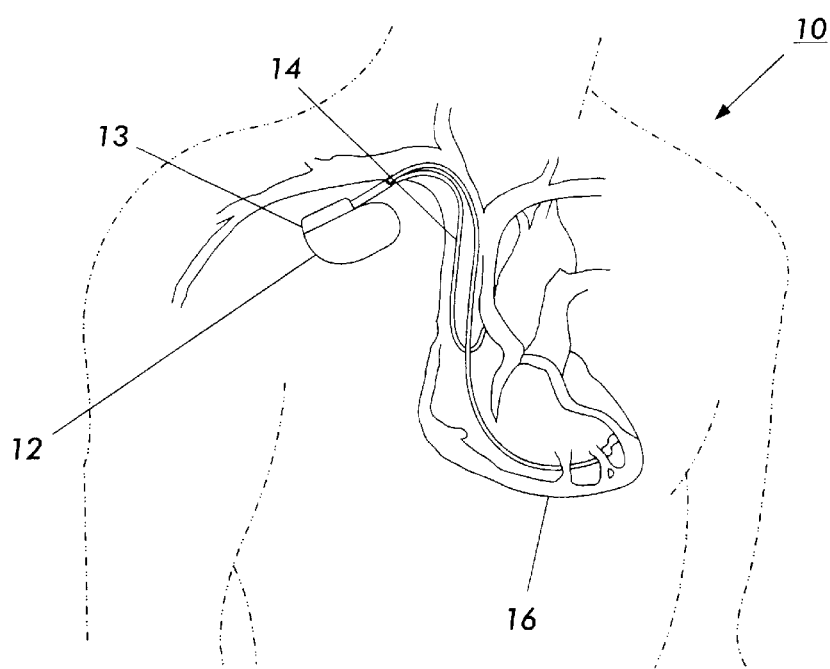
FIGS. 1 and 2 are illustrations of conventional techniques used to protect against electromagnetic interference.
Figure 2:
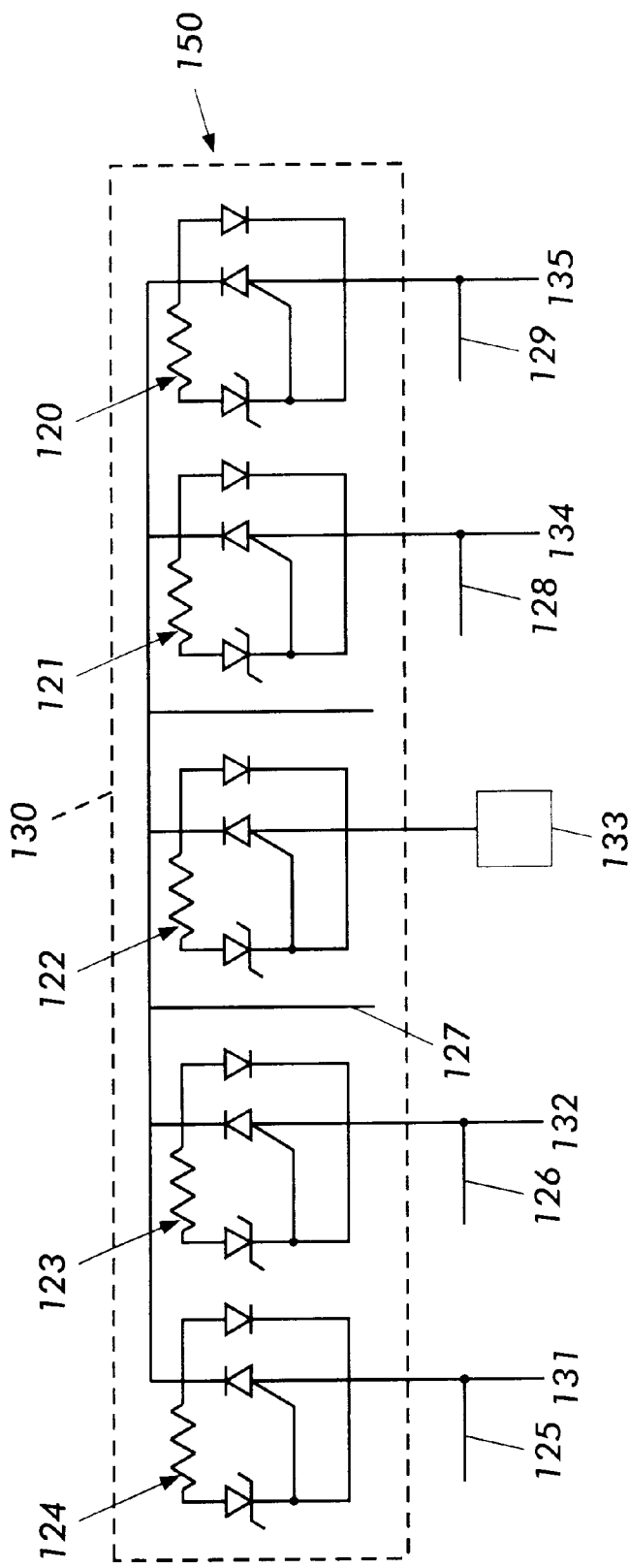
Figure 3:
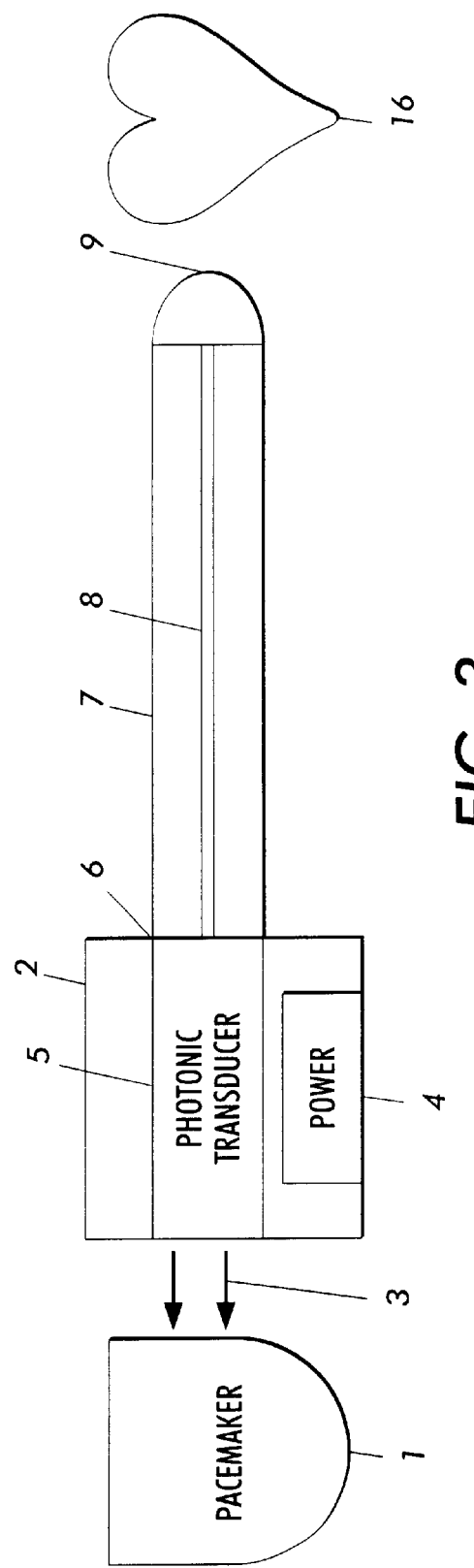
FIG. 3 is a block diagram of one embodiment of an MRI immune cardiac pacing system according to some or all of the concepts of the present invention.

FIG. 3 illustrates an MRI-compatible cardiac pacing system according to one embodiment of the present invention. The cardiac pacing system includes a cardiac pacer 1 that is designed to be located outside the body or implanted inside the body. The cardiac pacing system also includes an adapter 2, which can also be located outside the body or implanted inside the body, and is connected to the cardiac pacer by means of a first connector interface 3. Electrical pulses generated by the cardiac pacer are fed to the adapter 2 through the first connector interface 3. The adapter 2 can be connected to a proximal end 6 of a photonic catheter 7 by means of second connector interface (not shown).

In addition, the adapter 2 can be integral with the photonic catheter 7 so that a second connector interface is not required. Moreover, the adapter 2 can be connected to a proximal end of an EMI shielded electrical lead system by means of second connector interface (not shown). Lastly, the adapter 2 can be integral with the EMI shielded electrical lead system so that the second connector interface is not required.

The adapter enclosure 2 houses a self-contained electrical power source 4 and an electro-optical (photonic) transducer 5. The power source 4, which may include one or more batteries, serves as a power booster for the cardiac pacing system. The electro-optical (photonic) transducer 5 receives electrical pulses from the cardiac pacer 1, and converts them into optical signals. The optical signals are directed to the proximal end 6 of photonic catheter 7. The optical signals are transmitted through the optical conduction pathway 8 to the distal end 9 of the photonic catheter 7, and used to stimulate the heart 16.

Figure 20:
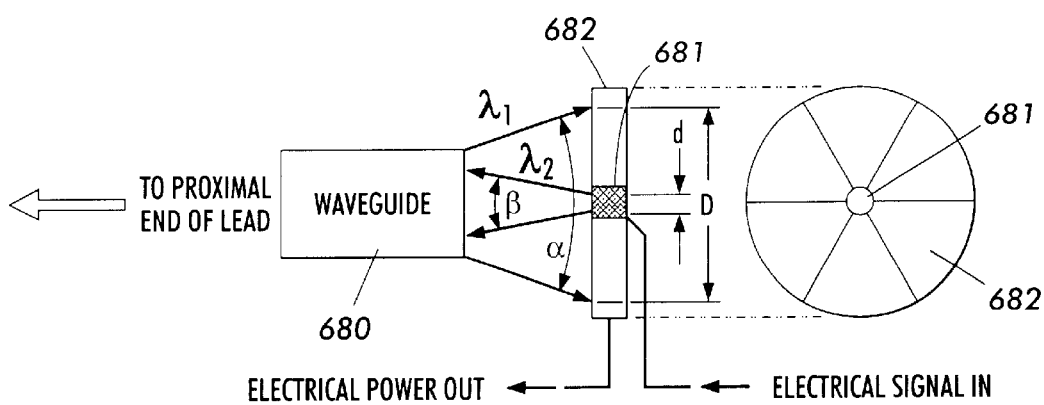
Figure 21:
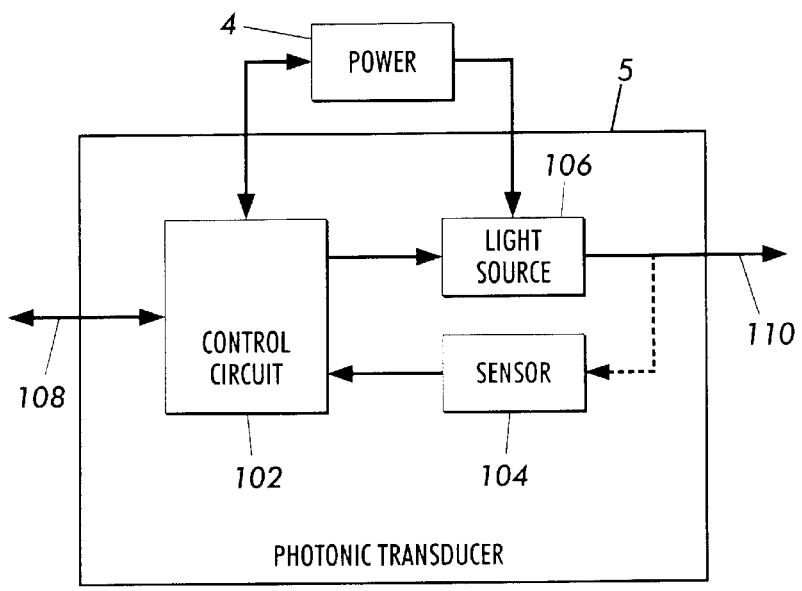
FIGS. 21 and 22 are detailed block diagrams of a photonic transducer according to the concepts of the present invention.

More specifically, the electro-optical (photonic) transducer 5, as illustrated in FIG. 21, includes a control circuit 102 that is electrically connected to the cardiac pacer through electrical connection 108. The control circuit 102 is further connected to a light source 106, preferably a laser source, and an optical sensor 104. The light source 106 and optical sensor 104 interact with a waveguide 110, which is part of a photonic catheter, in any of the manners described below with respect to FIGS. 5–20.

In response to pacing signals from the attached cardiac pacer, the control circuit 102 of FIG. 21 converts the electrical pacing signals to pulses of light or optical energy that represent the information conveyed in the original electrical pacing signals. The pacing information can be conveyed to the distal end of the photonic catheter using pulsewidth modulation of the light source 106 by the control circuit 102 controlling the "ON" and "OFF" time of the light source 106. Moreover, the pacing information can be conveyed to the distal end of the photonic catheter using pulse intensity modulation of the light source 106 by the control circuit 102 controlling the amount of power that the light source 106 receives from the power source 4, thereby controlling the intensity of the light pulse created by light source 106.

Optical sensor 104 receives biosensor feedback from the distal end of the photonic catheter, via encoded light pulses. The optical sensor 104 converts the encoded light pulses to electrical energy, which in turn is converted into electrical signals by the control circuit 102 so that the measured biofeedback can be properly conveyed back to the cardiac pacing device.

The adapter enclosure 2 also includes a shielding to shield the adapter and any circuits therein from electromagnetic interference. The shield may be a metallic sheath, a carbon composite sheath, or a polymer composite sheath to shield the adapter and any circuits therein from electromagnetic interference. The shield may be further covered with a biocompatible material wherein the biocompatible material may be a non-permeable diffusion resistant biocompatible material if the adapter is to be implanted.

Figure 4:
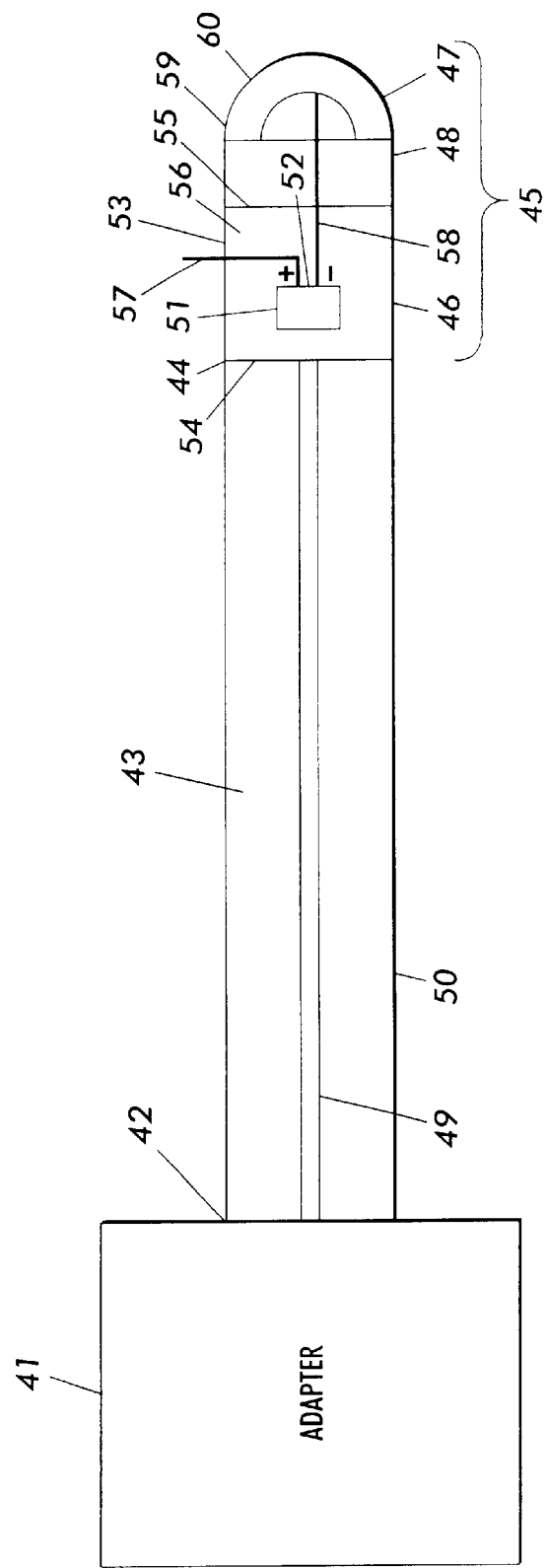
FIG. 4 is a block diagram of one embodiment of a photonic catheter according to some or all of the concepts of the present invention.

FIG. 4 illustrates in more detail the MRI compatible cardiac pacing system described in FIG. 3. The cardiac pacer is readily implemented to operate in a fixed-rate (VOO) mode. The cardiac pacing system includes an adapter 41, which is connected to the proximal end 42 of photonic catheter 43. A distal end 44 of photonic catheter 43 mounts a bipolar endocardial (or pericardial) electrode pair 45 that includes a second enclosure 46 and a third enclosure 47 separated by a short insulative spacer 48. Other electrode configurations could also be used.

The photonic catheter 43 includes an optical transmission pathway 49 surrounded by a protective outer covering 50. The optical transmission pathway 49 may be constructed with one or more fiber transmission elements that are conventionally made from glass or plastic fiber material, e.g., a fiber optic bundle. To avoid body fluid incompatibility problems, the protective outer covering 50, should be made from a biocompatible material, such as, but not limited to, silicone rubber, polyurethane, polyethylene, or other biocompatible polymer having the required mechanical and physiological properties. The protective outer covering 50 is thus a biocompatible covering.

Insofar as the photonic catheter 43 must be adapted for insertion into the body, the biocompatible covering 50 is preferably a very thin-walled elongated sleeve or jacket having an outside diameter on the order of one to five millimeters. This will render the photonic catheter 43 sufficiently slender to facilitate insertion thereof through a large vein, such as the external jugular vein.

The proximal end 42 of photonic catheter 43 is mounted on the adapter enclosure 41 using an appropriate connection. The optical conduction pathway 49 may extend into the adapter enclosure 41 for a short distance, where it terminates in adjacent relationship with the electro-optical (photonic) transducer in order to receive light energy therefrom.

Light emitted by the electro-optical (photonic) transducer is directed into the proximal end 42 of photonic catheter 43, and transmitted through the optical conduction pathway 49 to the second enclosure 46. Since the photonic catheter 43 is designed for optical transmission, it cannot develop magnetically induced or RF-induced electrical currents, as is the case with the metallic leads of conventional cardiac pacer catheters.

The second enclosure 46 houses an opto-electrical transducer 51, which converts light energy received from the distal end of photonic catheter 43 into electrical energy. The electrical output side 52 of the opto-electrical transducer 51 delivers electrical pulses that drive the cardiac pacer's electrode pair 45.

The second enclosure 46 is a hermetically sealed casing made from a non-magnetic metal, such as titanium, a titanium-containing alloy, platinum, a platinum-containing alloy, or any other suitable metal, including copper plated with a protective and compatible coating of the foregoing materials. Plated copper is especially suitable for the second enclosure 46 because it has a magnetic susceptibility approaching that of the human body, and will therefore minimize MRI image degradation. Note that the magnetic susceptibility of human body tissue is very low, and is sometimes diamagnetic and sometimes paramagnetic. As an alternative to using non-magnetic metals, the second enclosure 46 can be formed from an electrically conductive non-metal that preferably also has a very low magnetic susceptibility akin to that of the human body. Non-metals that best approach this condition include conductive composite carbon, and conductive polymers comprising silicone, polyethylene, or polyurethane.

The second enclosure 46 includes an outer wall 53 (in a preferred embodiment, the outer wall 53 is cylindrical, but any suitable shape may be utilized) and a pair of disk-shaped end walls 54 and 55. The end wall 54 is mounted to the distal end 44 of the photonic catheter 43 using an appropriate sealed connection that prevent body fluids from contacting the optical conduction pathway 49 and from entering the second enclosure 46. Although the photonic catheter 43 may feed directly from the adapter's enclosure 41 to the second enclosure 46, another arrangement would be to provide an optical coupling (not shown) at an intermediate location on the photonic catheter.

Due to the miniature size of the second enclosure 46, the optoelectrical transducer 51 needs to be implemented as a miniaturized circuit. However, such components are conventionally available from commercial electronic manufacturers. Note that the opto-electrical transducer 51 also needs to be adequately supported within the second enclosure 46. To that end, the second enclosure 46 can be filled with a support matrix material 56 that may be the same material used to form the photonic catheter's biocompatible covering.

As stated above, the second enclosure 46 represents part of an electrode pair 45 that delivers the electrical output of the pacemaker to a patient's heart. In particular, the electrode pair 45 is a tip/ring system and the second enclosure 46 is used as an endocardial (or pericardial) ring electrode thereof. A positive output lead 57 extending from the electrical output side 52 of the opto-electrical transducer 51 is electrically connected to the cylindrical wall 53 of the second enclosure 46, as by soldering, welding or the like. A negative output lead 58 extending from the electrical output side 52 of the opto-electrical transducer 51 is fed out of the second enclosure 46 and connected to a third enclosure 47, which functions as an endocardial tip electrode of the electric pair 45.

The third enclosure 47 can be constructed from the same non-metallic material, or non-metal material, used to form the second enclosure 46. Since it is adapted to be inserted in a patient's heart as an endocardial tip electrode, the third enclosure 47 has a generally bullet shaped tip 60 extending from a tubular base end 59. The base end 59 preferably has an outside diameter that substantially matches the diameter of the second enclosure 46 and the photonic catheter 43. Note that the base end 59 of the third enclosure 47 is open insofar as the third enclosure 47 does not house any critical components. Indeed, it mounts only the negative lead 58 that is electrically connected to the third enclosure's base end 59, as by soldering, welding, or the like.

The material used to form spacer 48 preferably fills the interior of the second enclosure 46 so that there are no voids and so that the negative lead 58 is fully captured therein.

As noted above, the adapter of the present invention provides an operational interface between a conventional medical assist device, such as a cardiac pacer, and an implanted photonic catheter. The photonic catheter can be used in a MRI environment to sense the biological conditions of particular tissue regions of a patient or to stimulate particular tissue regions of the patient. Depending upon the structure of the photonic catheter, the components of the adapter must be such as to correspond to the components of the photonic catheter to enable proper functionality. Examples of corresponding photonic catheter component and adapter component sets are illustrated in FIGS. 5 through 20.

Figure 5:
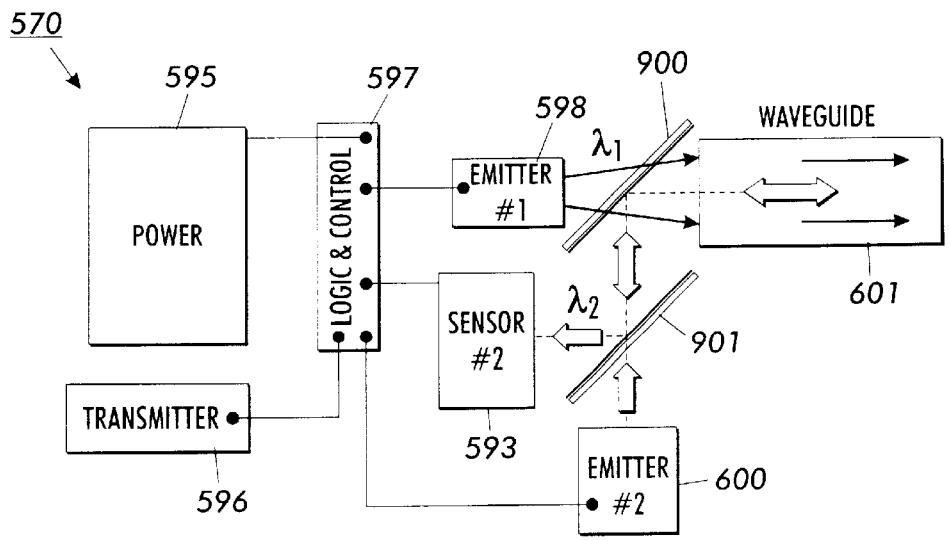
FIGS. 5 through 20 are schematics of various adapter transducers and corresponding distal end photonic catheter components according to some or all of the concepts of the present invention.
Figure 6:
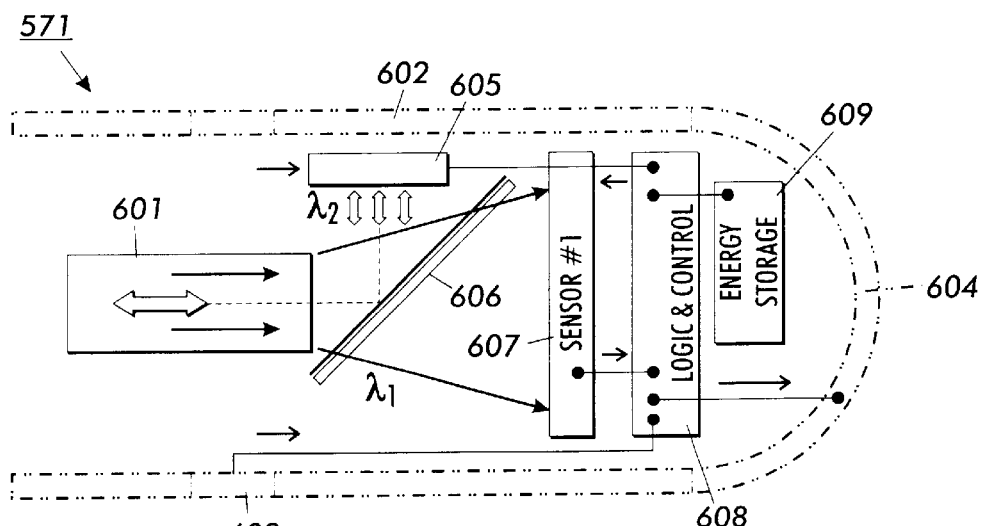

In FIGS. 5 and 6, the adapter includes a power supply 595 and logic and control unit 597 to enable emitter 598 to transmit radiation, preferably optical radiation at wavelength $\lambda_1$ through beam splitter 900 into waveguide 601. This radiation exits the waveguide 601 at the distal end of the photonic catheter and passes through beam splitter 606 to sensor 607 that converts the radiation to electrical energy.

The electrical energy is used to directly power functions at the distal end of photonic catheter 602, such as stimulation of internal body tissues and organs (e.g. pacing of cardiac tissues) through electrodes 604 and 603. The electrical energy is also used to power logic and control unit 608 or is stored in energy storage device 609 (e.g. a capacitor) for later use. Adapter located elements are electrically connected through electrical conductors. Distally located sensor 607, logic and control unit 608, energy storage device 609, and electrodes (604, 603) are electrically connected through electrically conductive elements.

A second emitter 600 in the adapter transmits radiation at wavelength $\lambda_2$ ($\lambda_2 \neq \lambda_1$) through beam splitter 901, off beam splitter 900, into waveguide 601 of the photonic catheter, to beam splitter 606 and optical attenuator 605 that is mounted on a mirror. The optical attenuator 605 is preferably made from materials such as liquid crystals whose optical transmission density is modulated by applied electrical voltage. The distally located logic and control unit 608 and optical attenuator 605 are powered either directly by excitation radiation or from energy stored in energy storage element 609.

The photonic catheter can also be used with electrodes 603 and 604 to capture physiological electrical signals or other measurements made by biosensors and converted to electrical signals from the patient and direct these electrical signals to logical and control unit 608 that uses electrical energy to modulate the optical transmission density of optical attenuator 605. Attenuated optical signals, originally emanating from emitter 600, are encoded with the electrical signals received by electrodes 603 and 604 by passing through the optical attenuator 605, reflect off mirror, travel back through the optical attenuator 605, reflect off beam splitter 606 and into waveguide 601 to beam splitters 900 and 901 in the adapter to sensor 599 that converts the encoded optical signal to an encoded electrical signal. Output from sensor 599 is sent to logic and control unit 597. This output is either utilized by logic and control unit 597 to control the radiation from emitter 598, which is typically at a high energy level and is used to stimulate distally located tissues and organs, or is relayed to transmitter 596 which relays this sensory information to external sources. It is noted that transmitter 596 may also be an electrical interface to a medical assist device.

Figure 7:
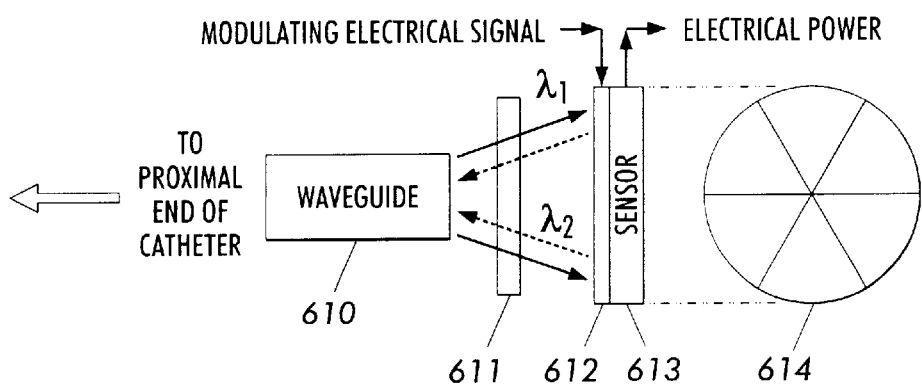

The embodiment illustrated in FIG. 7 is similar to the embodiment illustrated in FIGS. 5 and 6, with the exception that the optical attenuator 612 is mounted over the surface of the distally located sensor 613 to take advantage of the first surface reflectance of this sensor. Radiation emitted by waveguide 610 passes through optical attenuator 612 to sensor 613 that converts the radiation to electrical energy as previously described. Radiation emitted by waveguide 610 passes through optical attenuator 612 and reflects off the front surface of sensor 613. This reflected energy is collected by coupling lens 611 that directs the energy into waveguide 610 to a sensor within the adapter (not shown).

Figure 8:
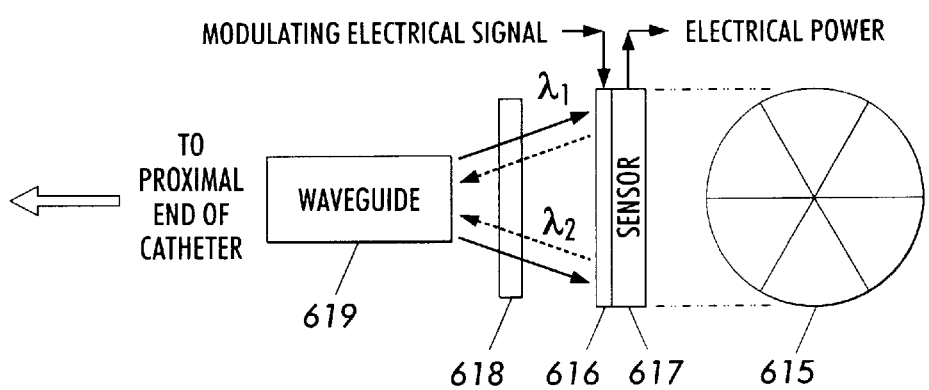

The embodiment illustrated in FIG. 8 is similar to the embodiment illustrated in FIGS. 5 and 6, with the exception that a variable reflectance optical reflector 616 is mounted over the surface of the distally located sensor 617. Radiation emitted by waveguide 619 passes through optical reflector 616 to sensor 617 that converts the radiation to electrical energy as previously described. Radiation emitted by waveguide 619 is reflected off optical reflector 616 and is collected by coupling lens 618 that directs the energy into waveguide 619. Preferably, the variable reflectance optical reflector 616 would be transparent to excitation radiation.

Figure 9:
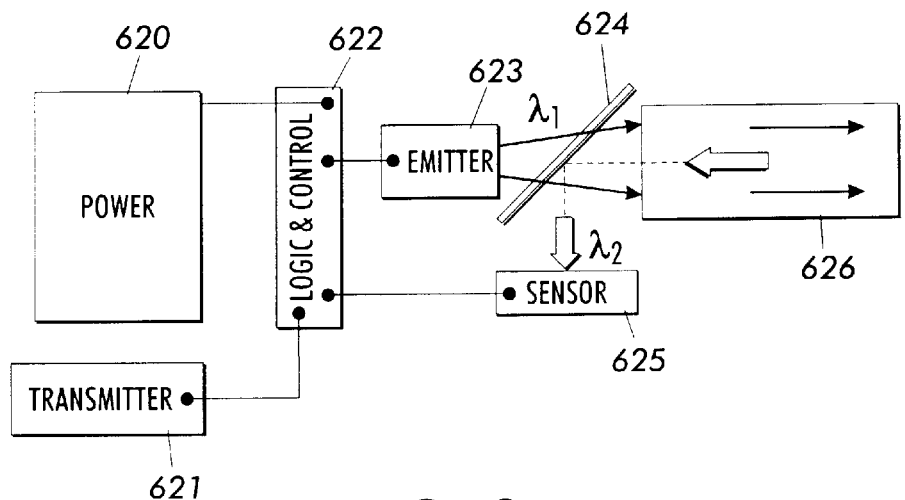
Figure 10:
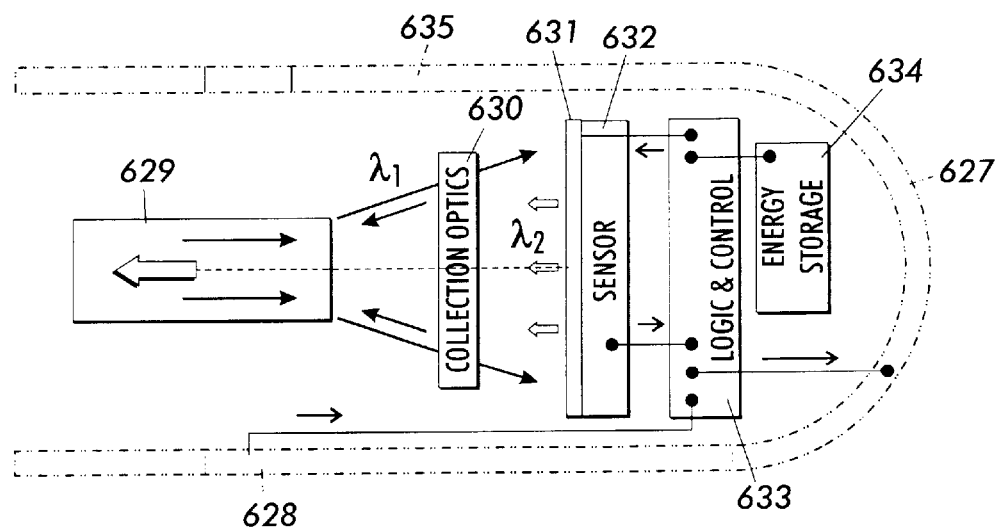

With respect to FIGS. 9 and 10, the adapter includes a power supply 620 and logic and control unit 622 to enable emitter 623 to transmit radiation, preferably optical radiation at wavelength $\lambda_1$ through beam splitter 624 into waveguide 626 of photonic catheter. This radiation exits the waveguide and passes through an on-axis variable intensity optical emitter 631 to sensor 632 that converts the radiation to electrical energy. The electrical energy is used to directly power functions at the distal end of photonic catheter 635, such as stimulation of internal body tissues and organs (e.g. pacing of cardiac tissues) through electrodes 627 and 628; to power logic and control unit 633; or to store in energy storage device 634 (e.g. a capacitor) for later use. Adapter located elements are electrically connected through conductors. Distally located sensor, logic and control unit, energy storage device, and electrodes are electrically connected through conductive elements.

Logic and control unit 633 receives sensor input from electrodes 627 and 628 and delivers an electrical potential to variable intensity optical emitter 631 causing it to emit optical radiation at wavelength $\lambda_2$ ($\lambda_2 \neq \lambda_1$) which is collected by coupling lens 630 and directed into waveguide 629, to beam splitter 624 and sensor 625. The distally located logic and control unit 633 and optical attenuator 631 are powered either directly by excitation radiation or from energy stored in energy storage element 634.

The photonic catheter can also be used with electrodes 627 and 628 to capture electrical signals from the patient and direct the captured electrical signals to logical and control unit 633 that uses electrical energy to modulate the variable intensity optical emitter 631. Optical signals, emanating from variable intensity optical emitter 631, are encoded with the electrical signals received by electrodes 627 and 628 and travel into waveguide 629 to beam splitter 624 to sensor 625 that converts the encoded optical signal to an encoded electrical signal. Output from sensor 625 is sent to logic and control unit 622. This output is either utilized by logic and control unit 622 to control the radiation from emitter 623, which is typically at a high energy level and is used to stimulate distally located tissues and organs, or is relayed to transmitter 621 which relays this sensory information to external sources. It is noted that transmitter 621 may also be an electrical interface to a medical assist device.

Figure 11:
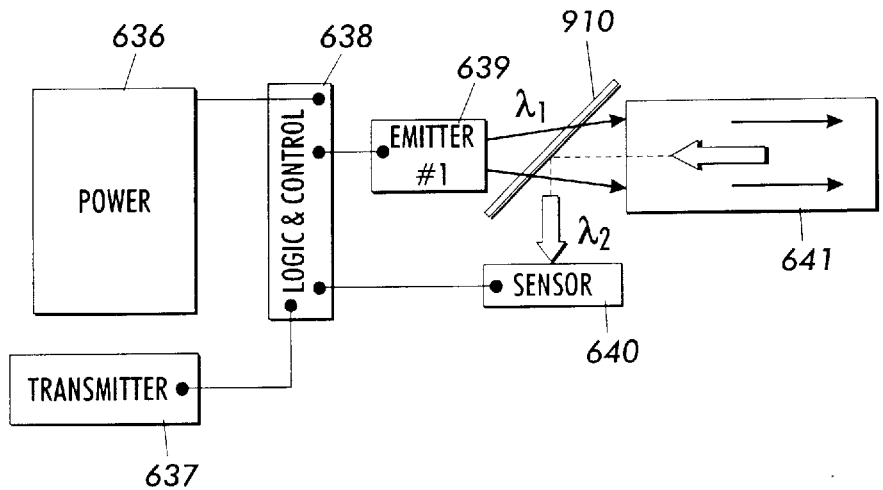
Figure 12:
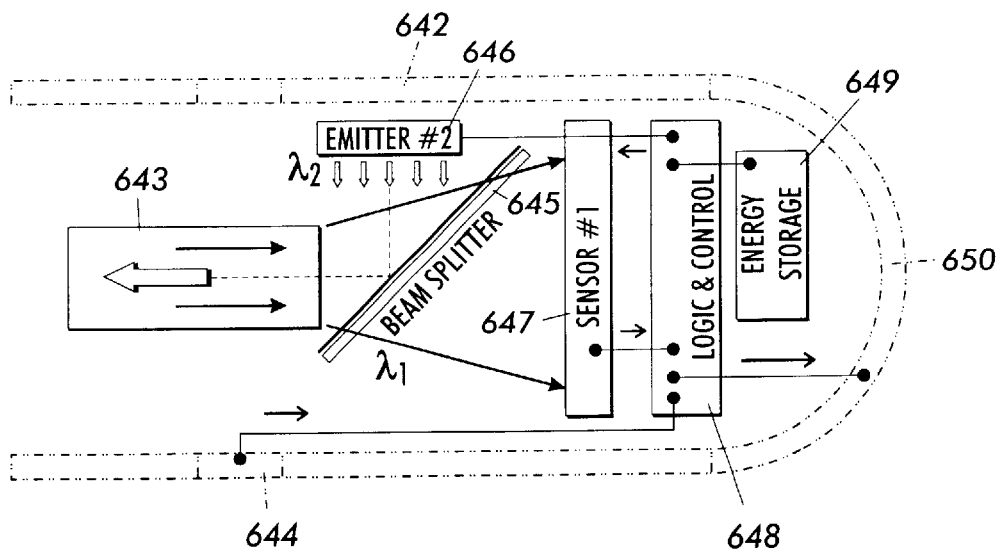

The embodiment illustrated in FIGS. 11 and 12 is similar to the embodiment illustrated in FIGS. 9 and 10, with the exception that the variable intensity optical emitter 646 is located off-axis. Power supply 636 and logic and control unit 638 enable emitter 639 to transmit radiation, preferably optical radiation at wavelength $\lambda_1$ through beam splitter 910 into waveguide 641. This radiation exits the waveguide 643 and passes through beam splitter 645 to sensor 647 that converts the radiation to electrical energy. The electrical energy is used to directly power functions at the distal end of lead 642, such as stimulation of internal body tissues and organs (e.g. pacing of cardiac tissues) through electrodes 650 and 644; power logic and control unit 648; or to be stored in energy storage device 649 (e.g. a capacitor) for later use.

Adapter located elements are electrically connected through conductors. Distally located sensor 647, logic and control unit 648, energy storage device 649, and electrodes 650 and 644 are electrically connected through conductive elements. Variable intensity emitter 646 transmits radiation at wavelength $\lambda_2$ ($\lambda_2 \neq \lambda_1$) off beam splitter 645 into waveguide 643 and off beam splitter 910 to sensor 640. Preferably, the variable intensity emitter 646 emits optical radiation when excited by an electrical potential, and is mounted upon a mirror to direct a greater percentage of emissions into waveguide 643.

A preferred application of the embodiment illustrated in FIGS. 11 and 12 uses electrodes 650 and 644 to capture electrical signals and direct them to logical and control unit 648 which delivers electrical energy to emitter 646 to emit optical radiation that is encoded with the electrical signals received by electrodes 650 and 644. The encoded optical signals are directed to beam splitter 645 and into waveguide 643 to sensor 640 that converts the encoded optical signal to an encoded electrical signal. Output from sensor 640 is sent to logic and control unit 638. This output is either utilized by logic and control unit 638 to control the radiation from emitter 639, which is typically at a high energy level (typically higher than radiation from emitter 646) and is used to stimulate distally located tissues and organs, or is relayed to transmitter 637 that relays this sensory information to external sources. It is noted that transmitter 637 may also be an electrical interface to a medical assist device.

Figure 13:
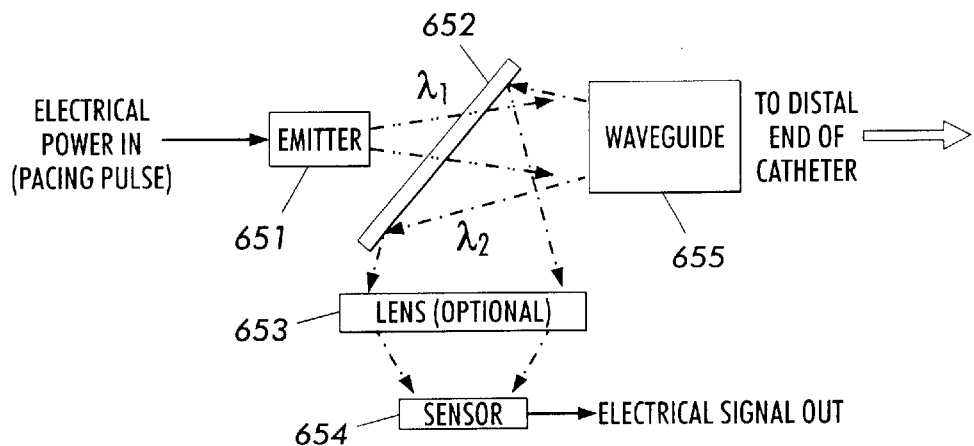
Figure 14:
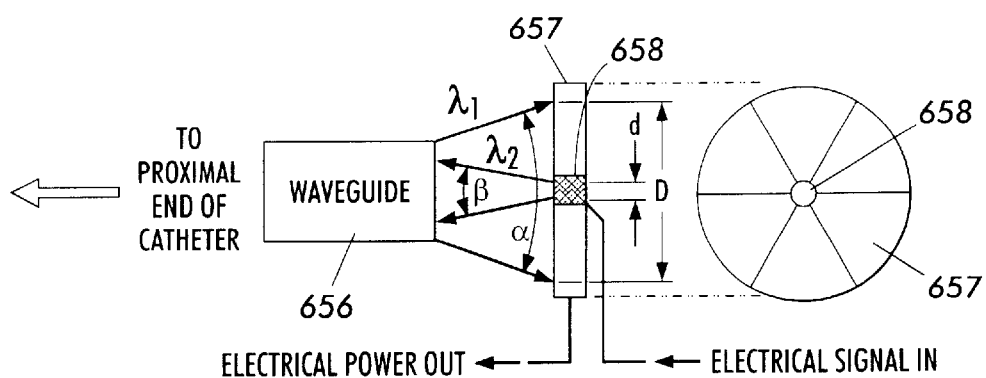

In FIGS. 13 and 14, radiation emitter 651, located in the adapter, transmits radiation, preferably optical radiation at wavelength $\lambda_1$ through beam splitter 652 into waveguide 655 of the photonic catheter. This radiation exits waveguide 656 at exit angle $\alpha$ and impinges upon sensor 657 that converts the radiation to electrical energy. The electrical energy is used as previously described.

A second emitter 658 located on or within sensor 657 transmits radiation at wavelength $\lambda_2$ ($\lambda_2 \neq \lambda_1$) at cone angle $\beta$ into waveguide 656 to beam splitter 652. The small size 'd' of emitter 658 relative to the larger size 'D' of sensor 658 and narrow radiation exit angle $\alpha$ and emission angle $\beta$ enable effective coupling of radiation from emitter 651 into sensor 657 and radiation from emitter 658 into waveguide 656. Optional coupling lens 653 collects and directs radiation to sensor 654. The distally located light source may be a solid-state laser, light emitting diode, or other source of optical energy.

Figure 15:
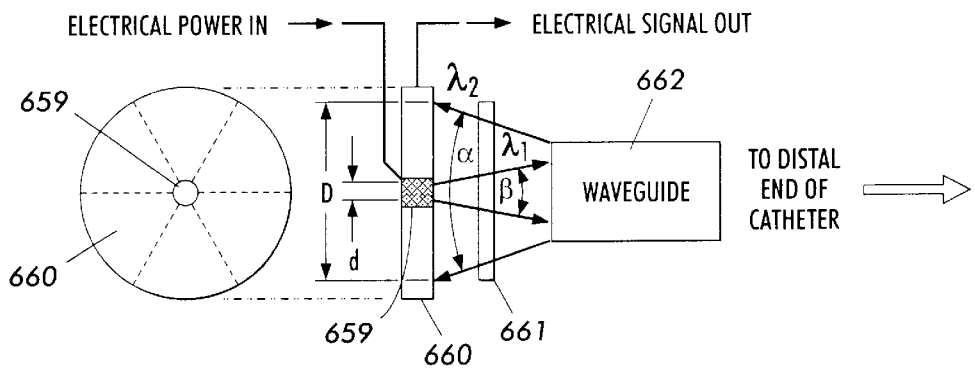
Figure 16:
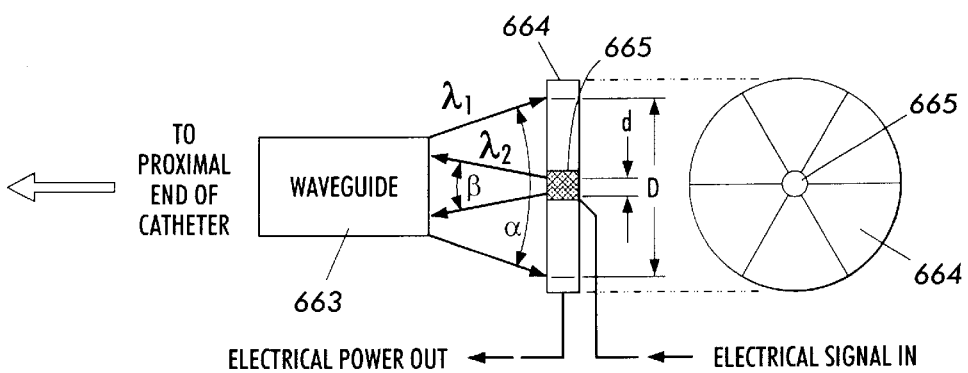

In FIGS. 15 and 16, radiation emitter 659, located in the adapter, transmits radiation, preferably optical radiation at wavelength $\lambda_1$ and exit angle $\beta_1$ through optional coupling lens 661 into waveguide 662. This radiation exits waveguide 663 at exit angle $\alpha_1$ and impinges upon sensor 664 that converts the radiation into electrical energy. The electrical energy is used as previously described.

A second emitter 665 located on or within sensor 664 transmits radiation at wavelength $\lambda_2$ at cone angle $\beta_2$ into waveguide 663. This radiation exits waveguide 662 at exit angle $\alpha_2$ onto sensor 660. Ideally, wavelength $\lambda_2 \neq \lambda_1$ so that optical reflections from coupling lens 661 or waveguide 662 do not interfere with radiation incident upon detector 660. The small sizes 'd' of emitters 659 and 665 relative to the larger sizes 'D' of sensors 660 and 664, combined with narrow radiation exit angles $\alpha_1$ and $\alpha_2$, and $\beta_1$ and $\beta_2$, enable effective coupling of radiation into waveguide (662, 663), and sensors 660 and 664.

Figure 17:
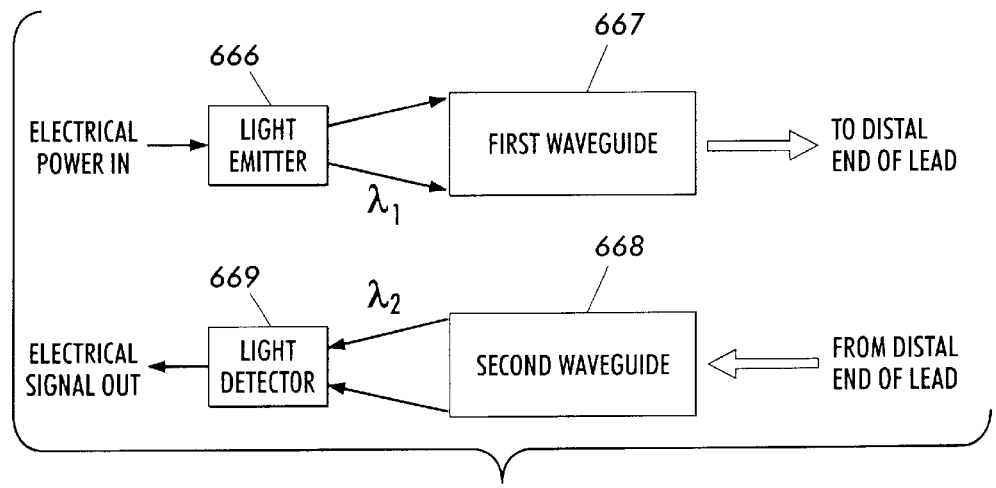
Figure 18:
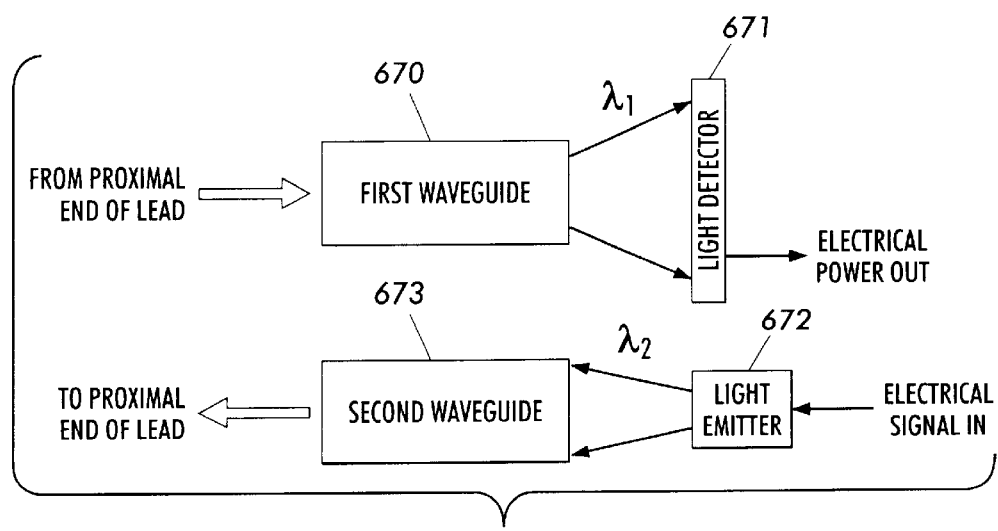

In FIGS. 17 and 18, radiation emitter 666, located in the adapter, transmits radiation, preferably optical radiation at wavelength $\lambda_1$ into waveguide 667. This radiation exits waveguide 670 and impinges upon sensor 671 that converts the radiation into electrical energy. The electrical energy is used as previously described.

A second distally located emitter 672 transmits radiation at wavelength $\lambda_2$ into waveguide 673. This radiation exits waveguide 668 onto proximally located sensor 669. Wavelength $\lambda_2$ may or may not be equal to wavelength $\lambda_1$. Light sources 666 and 672 include a solid-state laser or light emitting diode. Waveguides (667, 670) and (668, 673) are preferably included in the same lead assembly.

Figure 19:
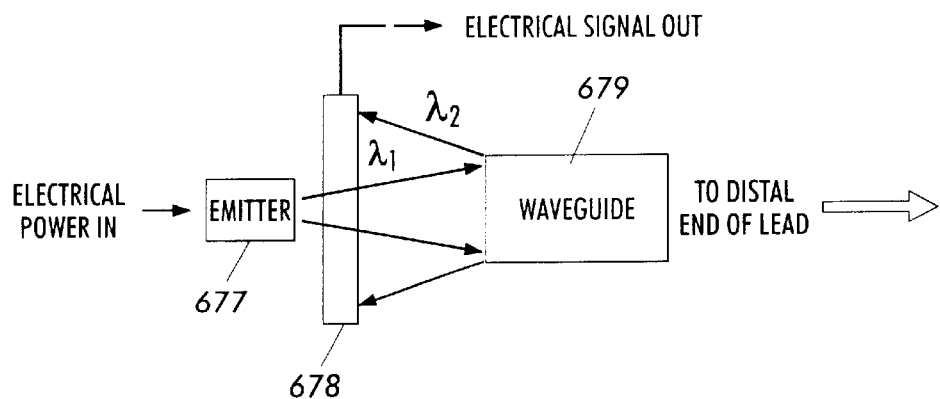

In FIGS. 19 and 20, a sensor 678, located in the adapter, transparent to certain wavelengths of optical radiation is used. Radiation emitter 677, located in the adapter, transmits radiation, preferably optical radiation at wavelength $\lambda_1$ through sensor 678 that is transparent to wavelength $\lambda_1$ into waveguide 679 and exiting at exit angle α to sensor 682 that converts the radiation to electrical energy. The electrical energy is used as previously described.

A second emitter 681 located on or within sensor 682 transmits radiation at wavelength $\lambda_2$ ($\lambda_2 \neq \lambda_1$) at cone angle β into waveguide 680 to proximally located sensor 678 where it is absorbed and converted into electrical energy. As before, the small size 'd' of emitter 681 relative to the larger size 'D' of sensor 682 and narrow radiation exit angle α and emission angle β enable effective coupling of radiation from emitter 677 into sensor 682 and radiation from emitter 681 into waveguide 680.

Notwithstanding the various implementations described above, it is desirable that the photonic lead and corresponding photonic adapter of the present invention electrically "look like" a conventional wire lead to a conventional pacemaker device. In other words, the photonic lead and corresponding photonic adapter of the present invention should be designed so that it is difficult for a conventional pacemaker device to tell, electronically, that the conventional pacemaker is connected to anything other than a conventional electrical wire lead.

Figure 22:
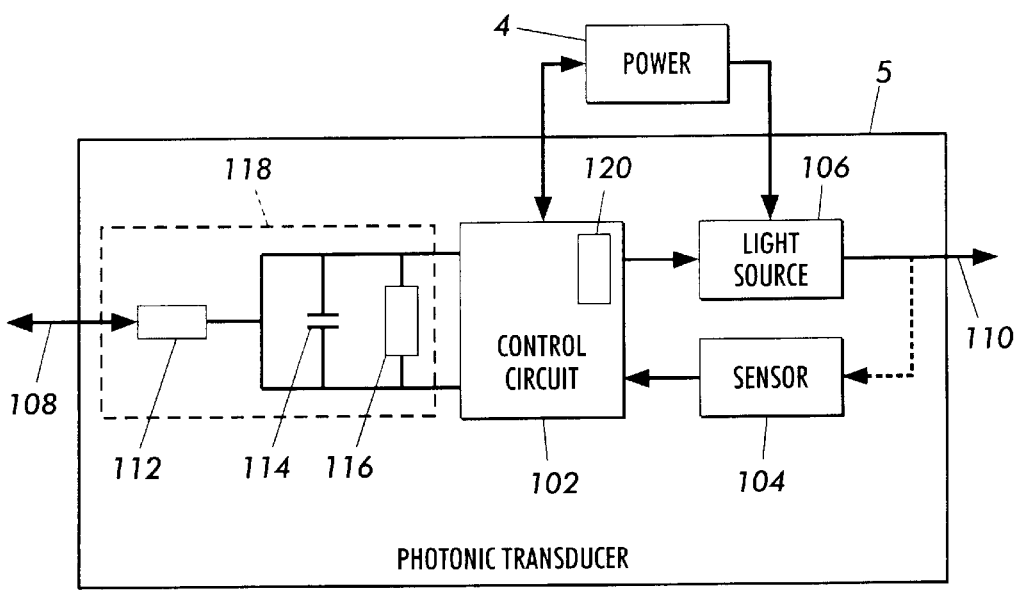

To enable this mimicking of conventional electrical wire lead, the photonic adapter of the present invention includes a predetermined number of resistors, inductors, and capacitors (preferably located within the photonic transducer) that are either preset or adjusted in a manner so that the combination of the photonic adapter and photonic lead mimic the resistance, inductance, and capacitance of a conventional wire lead that would have normally been attached to the pulse generator of a cardiac pacing device. In a preferred embodiment, as illustrated in FIG. 22, a pulse generator in a cardiac pacer drives an impedance load 118, within the photonic transducer 5, through electrical connection 108. The impedance load 118 includes a resistive load 116, preferably a 1K Ω resistor, which is connected in parallel to a capacitive load 114. The resistive load 116 is further connected in series with an inductive load 112. The impedance load 118 is connected to control circuit 102. The control circuit 102 is further connected to light source 106, preferably a laser source, and optical sensor 104. The light source 106 and optical sensor 104 interact with a waveguide 110, which is part of a photonic catheter, in any of the manners described above with respect to FIGS. 5–20.

In response to pacing signals from the attached cardiac pacer, the control circuit 102 of FIG. 22 converts the electrical pacing signals to pulses of light or optical energy that represent the information conveyed in the original electrical pacing signals. The pacing information can be conveyed to the distal end of the photonic catheter using pulsewidth modulation of the light source 106 by the control circuit 102 controlling the "ON" and "OFF" time of the light source 106. Moreover, the pacing information can be conveyed to the distal end of the photonic catheter using pulse intensity modulation of the light source 106 by the control circuit 102 controlling the amount of power that the light source 106 receives from the power source 4, thereby controlling the intensity of the light pulse created by light source 106.

Optical sensor 104 receives biosensor feedback from the distal end of the photonic catheter, via encoded light pulses. The optical sensor 104 converts the encoded light pulses to electrical energy, which in turn is converted into electrical signals by the control circuit 102 so that the measured biofeedback can be properly conveyed back to the cardiac pacing device.

The combination of the resistive load 116, capacitive load 114, and inductive load 112 mimic a conventional electrical wire lead's resistance, capacitance, and inductance (overall impedance).

Moreover, in another embodiment as illustrated in FIG. 22, a variable delay 120 is introduced into the photonic adapter to delay the transmission of the pacing signal from the pulse generator to the heart and the transmission of the feedback signal from the heart to the pulse generator. The variable delay 120 provides proper synchronization of the flow of information to and from the pulse generator.

It is further noted that conventional pacemaker leads are tested for continuity and proper interface with myocardium at installation and periodically after the installation procedure by measuring the impedance of the lead-myocardium system. This impedance will vary with time and physiological changes in the patient.

Figure 23:
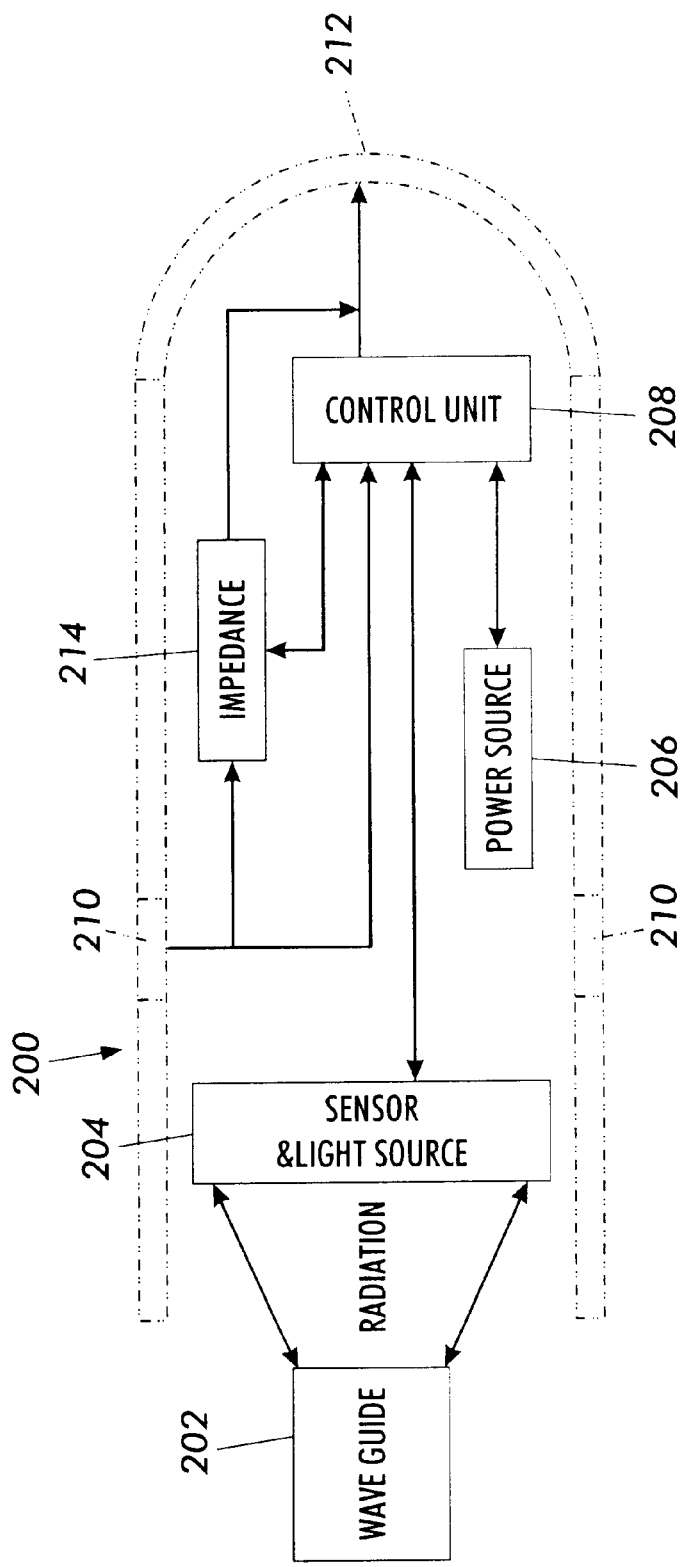
FIG. 23 is a detailed block diagram of an impedance sensing circuit in a photonic catheter according to the concepts of the present invention.

To realize this conventional testing in the present invention, as illustrated in FIG. 23, the distal end of a photonic catheter 200 includes an impedance measuring circuit 214. The impedance measuring circuit 214 is connected across a ring electrode 210 and a tip electrode 212. The impedance measuring circuit 214 sends small test signals to the electrodes 210 and 212 and measures the resistance of the circuit to determine the impedance of the lead-myocardium system. The measured impedance is fed to a control circuit 208, which is retained by the control circuit 208 to be used to modify the pacing energy applied to the heart in accordance with the measured impedance to ensure the proper amount of energy is delivered to the electrodes to effectuate proper pacing.

The measuring of the impedance of the lead-myocardium system and proper compensation therefore can be achieved by any conventional method. Examples of such conventional methods are disclosed in U.S. Pat. No. 5,775,742, to Schuelke et al.; U.S. Pat. No. 5.897,577 to Cinbis et al.; and U.S. Pat. No. 6,317,633 to Jorgenson et al. The entire content of these U.S. Patents (U.S. Pat. No. 5,775,742; U.S. Pat. No. 5.897,577; and U.S. Pat. No. 6,317,633) is hereby incorporated by reference.

In another embodiment, the distal end of the photonic lead is provided with the ability to measure impedance (impedance measuring circuit 214) at the electrode-myocardium interface, convert this into an encoded optical signal (sensor & light source 204), and transmit the encoded optical signal through waveguide 202 to the photonic adapter any change in impedance that takes place in a format that the pulse generator of the cardiac pacer will recognize as an accurate measure of actual change in interfacial impedance. The cardiac pacer can then respond using any conventional compensation method, such as those described above, to determine whether an adjustment in pacing pulse characteristics is required to ensure proper pacing.

In this embodiment, the photonic adapter has the additional capability in the control circuit of the photonic transducer to convert this change in electrical pacing pulse from the pulse generator into an equivalent change in pacing pulse delivered to the heart at the distal end of the photonic lead.

In another embodiment of the present invention, an enclosure provides physical securing and sealing to an outer casing of a medical assist device with which it electrically interfaces. In order to minimize manufacturing and inventory costs, to improve the convenience of surgical implantation, and to improve functional reliability, the photonic medical adapter device of the present invention may be manufactured with a single generic design, irrespective of its use with a wide variety of conventional, off-the-shelf medical assist devices that may have a variety of physical configurations and electrical connections.

By example, if the photonic medical assist device adapter of the present invention is an adapter to permit conventional electrical cardiac pacing systems to function in an MRI environment with the use of photonic technology previously described above, the photonic adapter device may have a single non-varying design, irrespective of its use in conjunction with a variety of electrical cardiac pacing products sold by a variety of manufacturers. To enable this single non-varying design, the present invention contemplates an adaptive bridge or adaptive interface, which acts as a passive electrical conduit between the conventional electrical cardiac pacing systems and the photonic adapter device described above.

In other words, a product-specific adaptive bridge or adaptive interface module provides passive electrical connection between a photonic adapter device, according to the concepts of the present invention, and the conventional cardiac pacer. The product-specific adaptive bridge or adaptive interface module provides for exact fitment, sealing, and bonding; on one aspect to the cardiac pacer and on the other aspect, to the photonic adapter device, according to the concepts of the present invention.

Figure 24:
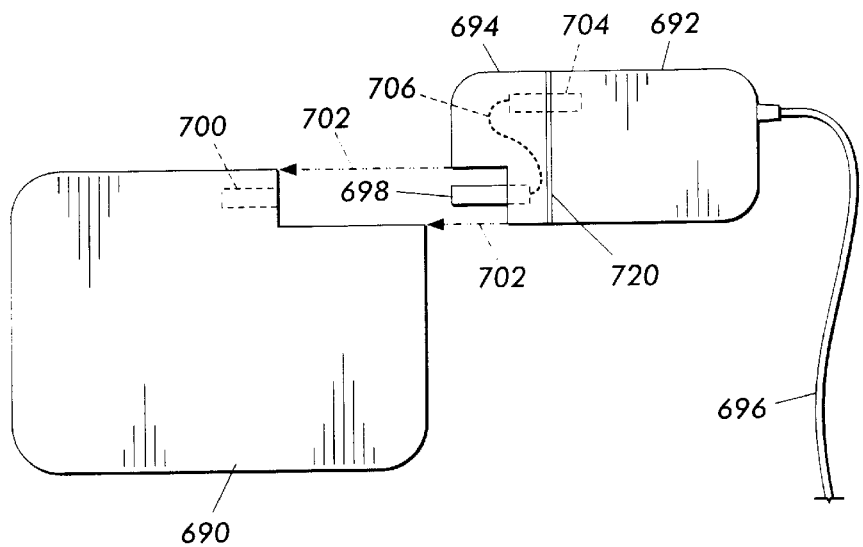
FIG. 24 is a schematic showing an adaptive bridge that provides electrical connection between a conventional medical assist device and a photonic catheter with an integral electric-optical adapter according to the concepts of the present invention.

FIG. 24 is a schematic of one embodiment, in which a generic photonic adapter device, according to the concepts of the present invention, provides all of the electronic, optical, control, and power functions, as well as providing an EMI-shielded and biologically sealed and compatible enclosure.

Referring specifically to FIG. 24, a conventional electrical pacemaker 690 is connected to a generic photonic adapter device 692, such as the photonic adapter devices illustrated in FIGS. 3 and 4, by way of product specific adaptive bridge or interface module 694. The photonic adapter device 692 communicates with the heart optically, in a manner as disclosed above, through photonic catheter 696. The product specific adaptive bridge or interface module 694 is connected electrically with the photonic adapter 692 by way of electrical contacts 704.

The product specific adaptive bridge or interface module 694 and the photonic adapter 692 are mechanically attached and biologically sealed at interface 720 by conventional means. These connections are preferably made during the last stages of device manufacture.

The product specific adaptive bridge or interface module 694 is further connected electrically to the conventional pacemaker 690 by way of electrical contacts 698 that communicate with electrical receptacle 700. These contacts 698 are specifically designed to match the specific model of the conventional pacemaker 690 that is being installed. Dashed lines 702 indicate the relationship between the product specific adaptive bridge or interface module 694 and the conventional pacemaker product 690 as mechanical assembly is performed, creating an interface that provides a mechanical attachment and biological seal.

Further, the mechanical geometry of the product specific adaptive bridge or interface module 694 is designed to exactly match the external geometry of the specific model of pacemaker 690 it is being used with and permits mechanical attachment and biological sealing at the interface by conventional means. The connections and sealing may be made during the last stages of overall device manufacture, or alternatively may be made at any time prior to implantation.

Electrical conductors 706 establish internal electrical connection between contacts 700 and contacts 704. Since the enclosures of the conventional pacemaker 690, the product specific adaptive bridge or interface module 694, and the photonic adapter 692 are individually shielded against electromagnetic interference and are in intimate contact, the overall assembly comprising elements 690, 692, and 694 will be unaffected by electromagnetic interference.

In like manner, the photonic adapter device 692 provides for bi-directional opto-electronic conversion of both sensory signals and pacing pulses in a manner that provides for exact replication of pacing pulses at the distal end of photonic catheter 696 and also provides for exact replication of sensory signals within the conventional pacemaker 690. Thus, the overall assembly comprising elements 690, 692, and 694 will provide the same functionality as would a photonic pacemaker system, but without the need to create a new product design.

In addition, the use of the photonic adapter of the present invention in conjunction with the product specific adaptive bridge or interface module 694, as described above, provides for a simple approach to provide photonic MRI safety and MRI compatibility to a wide range of commercially available conventional pacemaker models.

It is noted that the product specific adaptive bridge or interface module 694 of FIG. 24 may also include the impedance load, described above, in lieu of placement of the impedance load in the photonic adapter so as to mimic the impedance of a conventional electrical lead system.

Figure 25:
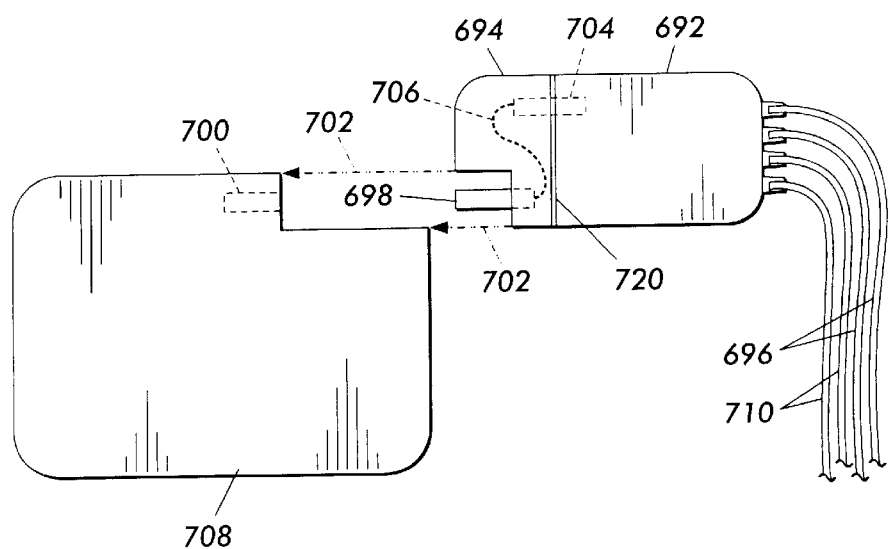
FIG. 25 is a schematic showing an adaptive bridge that provides electrical connection between a conventional medical assist device and a combined photonic catheter and EMI shielded electrical lead system with an integral electric-optical adapter according to the concepts of the present invention.

A further embodiment of the present invention is shown in FIG. 25. Referring to FIG. 25, a conventional electrical implantable cardioverter defibrillator (ICD) 708 is designed to carry out the multiple functions of sensing the heart, pacing the heart upon demand, and if necessary, defibrillating the heart with one or more electrical pulses that may be as high as 800 volts and having as much as 10 joules of energy or more.

While the photonic technology utilized in the photonic adapter of the present invention is well suited for conventional sensing and cardiac pacing functions, the energy level involved in defibrillation is far higher and would be difficult to realize with photonic technology.

Co-pending U.S. patent application Ser. No. 10/077,842, filed on Feb. 19, 2002, entitled "An Electromagnetic Interference Immune Tissue Invasive. System" discloses an EMI shielded electrical lead system that provides for electrical isolation of the pacemaker and the heart from the adverse effects of MRI fields, while permitting effective conduction of electrical pulses, such as a defibrillation pulse, if needed.

Referring again to FIG. 25, ICD 708 is physically affixed to a product specific adaptive bridge or interface module 694 and thence to a generic photonic adapter 692 in a manner identical to that described with respect to FIG. 24. However in the embodiment depicted in FIG. 25, electrical connection between ICD 708 and the product specific adaptive bridge or interface module 694 is made from multiple outputs 700, through multiple connectors 698, multiple electrical conductors 706, and multiple connectors 704.

In this embodiment, the circuitry in the photonic adapter 692 provides for a direct connection between outputs from ICD 708 to electrical leads 710. The electrical leads 710 having the material and construction described in above-referenced co-pending U.S. patent application Ser. No. 10/077,842.

This embodiment also provides for multi-chamber photonic pacing by providing bi-directional opto-electronic conversion between multiple multi-chamber sensing and pacing outputs 700 on ICD 708 and multiple photonic catheters 696 that may be placed at multiple locations on the heart in order to effect properly synchronized multi-chamber pacing of the heart.

It is noted that the product specific adaptive bridge or interface module 694 of FIG. 25 may also include the impedance load, described above, in lieu of placement of the impedance load in the photonic adapter so as to mimic the impedance of a conventional electrical lead system.

As will be evident to those skilled in the art, the approaches to physical and electrical attachment in the above embodiments, depicted in FIGS. 24 and 25, may be extended to all manner of commercially available cardiac assist devices and to any other electronic based implantable medical devices that may be rendered safe and effective in an MRI environment by implementation of a photonic catheter for one or more of its sensing or stimulation functions.

In summary, a medical assist device adapter, such as cardiac adapter, can be located outside or inside the patient's body and connected to a cardiac pacer and associated cardiac leads. The adapter comprises a housing, a shielding formed around the housing to shield the housing and any devices therein from electromagnetic interference; and interfaces to connect the adapter to a cardiac pacer and the adapter to implanted leads that correspond to a predetermined tissue region of the body. The housing may also include a power supply for providing electrical power to an electro-optical transducer, controller and other devices also residing in the housing.

The adapter may receive electrical pulses from the cardiac pacer or radio frequency signals if a transmitter/receiver is used. The electro-optical transducer converts the information from the cardiac pacer into optical signals, which are fed to one or more photonic leads and reconverted to electrical signals by an opto-electrical transducer located at the distal end of the photonic catheter to stimulate the tissue region, such as a heart.

The opto-electrical transducer also converts optical signals indicative of the functioning of the tissue region, such as a heart, into electric signals, which are used to control the operation of the medical assist device. The housing also includes a controller, which processes the feedback signals indicative of the functioning of the tissue region, and generates corresponding signals that are used as feedback for controlling the operation of the medical assist device.

The photonic catheter described above may be used for transmission of a signal to and from a body tissue of a vertebrate. The fiber optic bundle has a surface of non-immunogenic, physiologically compatible material and is capable of being permanently implanted in a body cavity or subcutaneously. The fiber optic bundle has a distal end for implantation at or adjacent to the body tissue and a proximal end. The proximal end is adapted to be coupled to and direct an optical signal source, and the distal end is adapted to be coupled to an optical stimulator. The fiber optic bundle delivers an optical signal intended to cause an optical stimulator coupled to the distal end to deliver an excitatory stimulus to a selected body tissue, such as a nervous system tissue region; e.g., spinal cord or brain. The stimulus causes the selected body tissue to function as desired.

The photonic catheter further includes a photoresponsive device for converting the light transmitted by the fiber optic bundle into electrical energy and for sensing variations in the light energy to produce control signals. In one embodiment a charge-accumulating device receives and stores the electrical energy produced by the photoresponsive device. A discharge control device, responsive to the control signals, directs the stored electrical energy from the charge-accumulating device to a cardiac assist device associated with a heart.

The photoresponsive device may include a charge transfer control circuit and a photodiode. The charge transfer control circuit controls a discharging of a photodiode capacitance in two separate discharge periods during an integration period of the photodiode such that a first discharge period of the photodiode capacitance provides the sensing of variations in the light energy to produce control signals and a second discharge period of the photodiode capacitance provides the converting the light transmitted by the photonic lead system into electrical energy. The first discharge period can be a shorter time duration that the time duration of the second discharge period. During the first discharge period, a control signal sensing circuit is connected to the photodiode, and during the second discharge period, the charge-accumulating device is connected to the photodiode. The charge-accumulating device may be a capacitor or a rechargeable battery.

The photonic catheter can also transmit between the primary device housing and the cardiac assist device, both power and control signals in the form of light. A photoresponsive device converts the light transmitted by the photonic lead system into electrical energy and to sense variations in the light energy to produce control signals. A charge-accumulating device receives and stores the electrical energy produced by the photoresponsive device, and a discharge control device, responsive to the control signals, directs the stored electrical energy from the charge-accumulating device to the cardiac assist device associated with the heart.

The photoresponsive device, in this embodiment, may include a charge transfer control circuit and a photodiode. The charge transfer control circuit controls a discharging of a photodiode capacitance in two separate discharge periods during an integration period of the photodiode such that a first discharge period of the photodiode capacitance provides the sensing of variations in the light energy to produce control signals and a second discharge period of the photodiode capacitance provides the converting the light transmitted by the photonic lead system into electrical energy. The first discharge period can be a shorter time duration that the time duration of the second discharge period. During the first discharge period, a control signal sensing circuit is connected to the photodiode, and during the second discharge period, the charge-accumulating device is connected to the photodiode. The charge-accumulating device may be a capacitor or a rechargeable battery.

The physical realization of the photodiode functions as light-detecting elements. In operation, the photodiode is first reset with a reset voltage that places an electronic charge across the capacitance associated with the diode. Electronic charge, produced by the photodiode when exposed to illumination, causes charge of the photodiode capacitance to dissipate in proportion to the incident illumination intensity. At the end of an exposure period, the change in photodiode capacitance charge is collected as electrical energy and the photodiode is reset.

Manipulating or adjusting the charge integration function of the photodiode can modify the creation of energy by the sensors. Charge integration function manipulation can be realized by changing of an integration time, $T_{int}$, for the photodiode. Changing the integration time, $T_{int}$, changes the start time of the charge integration period.

Integration time, $T_{int}$, is the time that a control signal is not set at a reset level. When the control signal is not at a reset value, the photodiode causes charge to be transferred or collected therefrom. The timing of the control signal causes charge to be transferred or collected from the photodiode for a shorter duration of time or longer duration of time. This adjustment can be used to manage the charge in the photodiode so that the photodiode does not become saturated with charge as well as to manage the current output of the sensor.

Another conventional way of manipulating the charge integration function is to use a stepped or piecewise discrete-time charge integration function. By using a stepped or piecewise discrete charge integration function, the charge in the photodiode can be further managed so that the photodiode does not become saturated with charge as well as to manage the current output of the photodiode.

Although most examples of the present invention refer to cardiac assist devices, the concepts of the present invention are readily applicable to any medical assist device that requires the use of implanted leads, such as photonic catheters.

While various examples and embodiments of the present invention have been shown and described, it will be appreciated by those skilled in the art that the spirit and scope of the present invention are not limited to the specific description and drawings herein, but extend to various modifications and changes all as set forth in the following claims.

What is claimed is:

1. A photonic adapter to provide an operational electrical interface between a medical assist device and a photonic catheter, comprising:
   a housing;
   an electrical interface to provide an operative connection between the photonic adapter and the medical assist device; and
   a photonic transducer to convert electrical energy from the medical assist device to optical energy, said optical energy being utilized by the photonic catheter.

2. The photonic adapter as claimed in claim 1, further comprising:
   an optical interface to provide an operative connection between the photonic adapter and the photonic catheter.

3. The photonic adapter as claimed in claim 1, further comprising a power source.

4. The photonic adapter as claimed in claim 1, wherein said electro-optical transducer comprises:
   a control circuit, operatively connected to said electrical interface, to convert electrical energy from the medical assist device into control signals; and
   a light source, operatively connected to said control circuit, to provide optical energy in response to said control signals.

5. The photonic adapter as claimed in claim 4, wherein said electro-optical transducer further comprises:
   a sensor, operatively connected to said control circuit, for receiving optical energy representing sensed conditions at a distal end of the photonic catheter and converting the optical energy into an electrical signal representing the sensed conditions at a distal end of the photonic catheter.

6. The photonic adapter as claimed in claim 4, wherein said light source is a laser.

7. The photonic adapter as claimed in claim 1, wherein the medical assist device is a cardiac assist device.

8. The photonic adapter as claimed in claim 1, further comprising:
   an impedance load to mimic an impedance of an electrical lead.

9. A photonic adapter to provide an operational transmitter/receiver interface between a medical assist device and a photonic catheter, comprising:
   a housing;
   a transmitter/receiver interface to provide an operative communication connection between the adapter and the medical assist device; and
   a transducer to convert information from the medical assist device into optical energy.

10. The photonic adapter as claimed in claim 9, wherein said transducer comprises:
    a control circuit, operatively connected to said transmitter/receiver interface, to convert information from the medical assist device into control signals; and
    a light source, operatively connected to said control circuit, to provide optical energy in response to said control signals.

11. The photonic adapter as claimed in claim 10, wherein said transducer further comprises:
    a sensor, operatively connected to said control circuit, for receiving optical energy representing sensed conditions at a distal end of the photonic catheter and converting the optical energy into an electrical signal representing the sensed conditions at a distal end of the photonic catheter.

12. An electromagnetic radiation immune medical assist system, comprising:
    a medical assist device;
    a photonic lead having a proximal end and a distal end; and
    an adapter to operatively connect said medical assist device with said photonic catheter;
    said adapter including,
        a housing,
        an interface to provide an operative communication connection between said adapter and said medical assist device, and
        a transducer to convert information from said medical assist device into optical energy.

13. The electromagnetic radiation immune medical assist system as claimed in claim 12, wherein:
    said transducer includes,
        a control circuit operatively connected to said interface, to convert information from said medical assist device into control signals, and a light source, operatively connected to said control circuit, to provide optical energy in response to said control signals; and said photonic catheter including a waveguide between a proximal end and distal end of said photonic lead.

14. An adaptive bridge for providing an interface between a photonic adapter and a medical assist device, comprising:

a first interface to provide an electrical connection between the adaptive bridge and the medical assist device;

a second interface to provide an electrical connection between the adaptive bridge and the photonic adapter; and a passive electrical lead to provide an electrical conduit between said first interface and said second interface.

15. The adaptive bridge as claimed in claim 14, further comprising:

an impedance load to mimic an impedance of an electrical lead.

16. The adaptive bridge as claimed in claim 14, wherein said first interface provides mechanical attachment and a biological seal between the adaptive bridge and the medical assist device.

17. The adaptive bridge as claimed in claim 14, wherein said second interface provides mechanical attachment and a biological seal between the adaptive bridge and the photonic adapter.

18. A medical assist system, comprising:

a medical assist device;

a photonic adapter; and an adaptive bridge for providing an interface between said photonic adapter and said medical assist device.

19. The medical assist system as claimed in claim 18, wherein said photonic adapter includes:

a housing;

an electrical interface to provide an operative connection between said photonic adapter and said adaptive bridge; and a photonic transducer to convert electrical energy from said adaptive bridge to optical energy, said optical energy being utilized by the photonic catheter.

20. The medical assist system as claimed in claim 19, wherein said photonic transducer includes:

a control circuit, operatively connected to said electrical interface, to convert electrical energy from said photonic adapter into control signals;

a light source, operatively connected to said control circuit, to provide optical energy in response to said control signals; and:

a sensor, operatively connected to said control circuit, for receiving optical energy representing sensed conditions at a distal end of the photonic catheter and converting the optical energy into an electrical signal representing the sensed conditions at a distal end of the photonic catheter.

21. The medical assist system as claimed in claim 18, wherein said adaptive bridge includes:

a first interface to provide an electrical connection between said adaptive bridge and said medical assist device;

a second interface to provide an electrical connection between said adaptive bridge and said photonic adapter; and a passive electrical lead to provide an electrical conduit between said first interface and said second interface.

* * * * *